(12) United States Patent
Rousseau

(10) Patent No.: US 8,307,831 B2
(45) Date of Patent: Nov. 13, 2012

(54) IMPLANT SYSTEMS AND METHODS FOR TREATING OBSTRUCTIVE SLEEP APNEA

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 205 days.

(21) Appl. No.: 12/404,377

(22) Filed: Mar. 16, 2009

(65) Prior Publication Data

US 2010/0234946 A1    Sep. 16, 2010

(51) Int. Cl.
*A61F 5/56* (2006.01)
(52) U.S. Cl. .................. 128/848; 602/902; 128/859
(58) Field of Classification Search .............. 128/848, 128/897–899, 859; 602/902; 606/157
See application file for complete search history.

(56) References Cited

U.S. PATENT DOCUMENTS

| | | | |
|---|---|---|---|
| 3,123,077 A | 3/1964 | Alcamo | |
| 3,378,010 A * | 4/1968 | Codling et al. | ............... 606/157 |
| 4,069,825 A | 1/1978 | Akiyama | |
| 4,557,264 A | 12/1985 | Hinsch | |
| 4,839,215 A | 6/1989 | Starling et al. | |
| 4,881,939 A | 11/1989 | Newman | |
| 4,950,285 A | 8/1990 | Wilk | |
| 5,053,047 A | 10/1991 | Yoon | |
| 5,123,913 A | 6/1992 | Wilk et al. | |
| 5,269,783 A | 12/1993 | Sander | |
| 5,284,161 A | 2/1994 | Karell | |
| 5,311,028 A | 5/1994 | Glavish | |
| 5,393,984 A | 2/1995 | Glavish | |
| 5,483,077 A | 1/1996 | Glavish | |
| 5,609,559 A | 3/1997 | Weitzner | |
| 5,683,417 A | 11/1997 | Cooper | |
| 5,704,895 A | 1/1998 | Scott | |
| 5,792,067 A | 8/1998 | Karell | |
| 5,843,077 A | 12/1998 | Edwards | |
| 5,931,855 A | 8/1999 | Buncke | |
| 6,161,541 A | 12/2000 | Woodson | |
| 6,241,747 B1 | 6/2001 | Ruff | |
| 6,250,307 B1 | 6/2001 | Conrad et al. | |
| 6,431,174 B1 | 8/2002 | Knudson et al. | |

(Continued)

FOREIGN PATENT DOCUMENTS

JP    2003265621    9/2003

(Continued)

OTHER PUBLICATIONS

Harries, et al., "The Surgical treatment of snoring," Journal of Laryngology and Otology, pp. 1105-1106 (1996).

(Continued)

*Primary Examiner* — Patricia Bianco
*Assistant Examiner* — Kari Petrik

(57) ABSTRACT

A system for treating obstructive sleep apnea includes a body implantable in a soft palate, and a fastening element at a proximal end of the body for connecting the body with a hard palate. In one embodiment, the body is curved and has a convex top surface and a concave bottom surface. The curved body is adapted to support and/or change the shape of the soft palate for minimizing the likelihood of airway obstructions during sleep. The fastening element, secureable to the hard palate, includes at least one barb adapted to engage the hard palate for anchoring the body to the hard palate. In one embodiment, the body has a surface adapted to promote tissue in-growth. The implant body may be made of materials including nitinol, stainless steel, biocompatible polymers, temperature-sensitive materials, and shape memory materials.

15 Claims, 18 Drawing Sheets

U.S. PATENT DOCUMENTS

| | | | |
|---|---|---|---|
| 6,432,437 B1 | 8/2002 | Hubbard | |
| 6,457,472 B1 | 10/2002 | Schwartz et al. | |
| 6,513,530 B2 | 2/2003 | Knudson et al. | |
| 6,523,542 B2 | 2/2003 | Knudson et al. | |
| 6,578,580 B2 | 6/2003 | Conrad et al. | |
| 6,589,549 B2 | 7/2003 | Shih et al. | |
| 6,599,310 B2 | 7/2003 | Leung et al. | |
| 6,627,600 B2 | 9/2003 | Boutignon | |
| 6,634,362 B2 | 10/2003 | Conrad et al. | |
| 6,638,284 B1 | 10/2003 | Rousseau et al. | |
| 6,716,251 B1 | 4/2004 | Asius et al. | |
| 6,742,524 B2 | 6/2004 | Knudson et al. | |
| 6,755,868 B2 | 6/2004 | Rousseau | |
| 6,800,082 B2 | 10/2004 | Rousseau | |
| 6,899,105 B2 | 5/2005 | Krueger et al. | |
| 6,955,172 B2 | 10/2005 | Nelson et al. | |
| 6,981,944 B2 | 1/2006 | Jamiolkowski et al. | |
| 7,017,582 B2 | 3/2006 | Metzger et al. | |
| 7,056,331 B2 | 6/2006 | Kaplan et al. | |
| 7,135,189 B2 | 11/2006 | Knapp | |
| 7,146,981 B2 | 12/2006 | Knudson et al. | |
| 7,166,570 B2 | 1/2007 | Hunter et al. | |
| 7,213,599 B2 | 5/2007 | Conrad et al. | |
| 7,237,554 B2 | 7/2007 | Conrad et al. | |
| 7,261,702 B1 | 8/2007 | Alexandre et al. | |
| 7,288,075 B2 | 10/2007 | Parihar et al. | |
| 7,297,102 B2 | 11/2007 | Smith et al. | |
| 7,322,993 B2 | 1/2008 | Metzger et al. | |
| 7,337,781 B2 | 3/2008 | Vassallo | |
| 7,360,432 B2 | 4/2008 | Lehtonen | |
| 7,360,542 B2 | 4/2008 | Nelson et al. | |
| 7,367,340 B2 | 5/2008 | Nelson et al. | |
| 7,401,611 B2 | 7/2008 | Conrad et al. | |
| 7,601,164 B2 | 10/2009 | Wu | |
| 7,669,603 B2 | 3/2010 | Knudson et al. | |
| 7,806,908 B2 | 10/2010 | Ruff | |
| 7,857,829 B2 | 12/2010 | Kaplan et al. | |
| 2001/0037133 A1 | 11/2001 | Knudson et al. | |
| 2003/0004579 A1 | 1/2003 | Rousseau et al. | |
| 2003/0149445 A1 | 8/2003 | Knudson et al. | |
| 2003/0149447 A1 | 8/2003 | Morency et al. | |
| 2004/0020492 A1 | 2/2004 | Dubrul et al. | |
| 2004/0020498 A1 | 2/2004 | Knudson et al. | |
| 2004/0028676 A1 | 2/2004 | Klein et al. | |
| 2004/0102796 A1 | 5/2004 | Hill et al. | |
| 2004/0139975 A1 | 7/2004 | Nelson et al. | |
| 2004/0149290 A1 | 8/2004 | Nelson et al. | |
| 2004/0153127 A1 | 8/2004 | Gordon et al. | |
| 2005/0082452 A1 | 4/2005 | Kirby | |
| 2005/0092334 A1 | 5/2005 | Conrad et al. | |
| 2005/0115572 A1 | 6/2005 | Brooks et al. | |
| 2005/0199248 A1 | 9/2005 | Pflueger et al. | |
| 2005/0203576 A1 | 9/2005 | Sulamanidze et al. | |
| 2005/0251255 A1 | 11/2005 | Metzger et al. | |
| 2005/0267321 A1 | 12/2005 | Shadduck | |
| 2005/0267532 A1 | 12/2005 | Wu | |
| 2005/0267571 A1 | 12/2005 | Spence et al. | |
| 2005/0279365 A1 | 12/2005 | Armijo et al. | |
| 2006/0083767 A1 | 4/2006 | Deusch et al. | |
| 2006/0093644 A1 | 5/2006 | Quelle et al. | |
| 2006/0150986 A1 | 7/2006 | Roue et al. | |
| 2006/0185673 A1 | 8/2006 | Critzer et al. | |
| 2006/0206917 A1 | 9/2006 | Morsi | |
| 2006/0207608 A1 | 9/2006 | Hirotsuka et al. | |
| 2006/0228391 A1 | 10/2006 | Seyedin et al. | |
| 2006/0241339 A1 | 10/2006 | Cook et al. | |
| 2006/0266369 A1 | 11/2006 | Atkinson et al. | |
| 2006/0289015 A1 | 12/2006 | Boucher et al. | |
| 2007/0000497 A1* | 1/2007 | Boucher et al. | 128/848 |
| 2007/0005109 A1 | 1/2007 | Popadiuk et al. | |
| 2007/0005110 A1 | 1/2007 | Collier et al. | |
| 2007/0102010 A1 | 5/2007 | Lemperle et al. | |
| 2007/0110788 A1 | 5/2007 | Hissong et al. | |
| 2007/0119463 A1 | 5/2007 | Nelson et al. | |
| 2007/0123996 A1 | 5/2007 | Sugaya et al. | |
| 2007/0144531 A1 | 6/2007 | Tomas et al. | |
| 2007/0144534 A1 | 6/2007 | Mery et al. | |
| 2007/0144535 A1* | 6/2007 | Hegde et al. | 128/848 |
| 2007/0190108 A1 | 8/2007 | Datta et al. | |
| 2007/0204866 A1 | 9/2007 | Conrad et al. | |
| 2007/0209665 A1 | 9/2007 | Gillis et al. | |
| 2007/0227545 A1* | 10/2007 | Conrad et al. | 128/848 |
| 2007/0233276 A1 | 10/2007 | Conrad et al. | |
| 2007/0246052 A1 | 10/2007 | Hegde et al. | |
| 2007/0256693 A1 | 11/2007 | Paraschac et al. | |
| 2007/0261701 A1 | 11/2007 | Sanders | |
| 2007/0270631 A1 | 11/2007 | Nelson et al. | |
| 2007/0272257 A1 | 11/2007 | Nelson et al. | |
| 2007/0295338 A1 | 12/2007 | Loomas et al. | |
| 2007/0295340 A1 | 12/2007 | Buscemi | |
| 2008/0023012 A1 | 1/2008 | Dineen et al. | |
| 2008/0035160 A1 | 2/2008 | Woodson et al. | |
| 2008/0066764 A1 | 3/2008 | Paraschac et al. | |
| 2008/0066765 A1 | 3/2008 | Paraschac et al. | |
| 2008/0066767 A1 | 3/2008 | Paraschac et al. | |
| 2008/0066769 A1 | 3/2008 | Dineen et al. | |
| 2008/0078411 A1 | 4/2008 | Buscemi et al. | |
| 2008/0146868 A1 | 6/2008 | Henri Robert et al. | |
| 2008/0167614 A1 | 7/2008 | Tolkowsky et al. | |
| 2008/0208265 A1 | 8/2008 | Frazier et al. | |
| 2008/0221684 A1 | 9/2008 | Nelson et al. | |
| 2009/0025734 A1 | 1/2009 | Doelling et al. | |
| 2009/0078411 A1 | 3/2009 | Kenison et al. | |
| 2010/0132719 A1 | 6/2010 | Jacobs et al. | |
| 2010/0137794 A1 | 6/2010 | Knudson et al. | |
| 2010/0137905 A1 | 6/2010 | Weadock et al. | |
| 2010/0163056 A1* | 7/2010 | Tschopp et al. | 128/848 |
| 2010/0234946 A1 | 9/2010 | Rousseau | |
| 2011/0100376 A1 | 5/2011 | Rousseau | |
| 2011/0100377 A1 | 5/2011 | Weadock et al. | |
| 2011/0100378 A1 | 5/2011 | Rousseau | |
| 2011/0144558 A1 | 6/2011 | Rousseau | |
| 2011/0174315 A1* | 7/2011 | Zhang et al. | 128/848 |

FOREIGN PATENT DOCUMENTS

| | | |
|---|---|---|
| WO | WO 99/00058 A1 | 1/1999 |
| WO | WO 00/66050 | 11/2000 |
| WO | WO 01/021107 A1 | 3/2001 |
| WO | WO 2004/021870 | 3/2004 |
| WO | WO 2004/060311 | 7/2004 |
| WO | WO 2004/084709 | 10/2004 |
| WO | WO 2005/046554 | 5/2005 |
| WO | WO 2005/051292 A2 | 6/2005 |
| WO | WO 2005/082452 A1 | 9/2005 |
| WO | WO 2005/122954 A1 | 12/2005 |
| WO | WO 2006/012188 | 2/2006 |
| WO | WO 2006012188 | 2/2006 |
| WO | WO 2006/072571 | 7/2006 |
| WO | WO 2006/108145 A1 | 10/2006 |
| WO | WO 2007/056583 A1 | 5/2007 |
| WO | WO 2007/075394 | 7/2007 |
| WO | 2007134005 | 11/2007 |
| WO | WO 2007/132449 | 11/2007 |
| WO | WO 2007/146338 A2 | 12/2007 |
| WO | WO 2007/149469 | 12/2007 |
| WO | WO 2008/118913 A2 | 10/2008 |
| WO | WO 2009/023256 A2 | 2/2009 |
| WO | WO 2009/036094 | 3/2009 |
| WO | WO 2010/065341 A1 | 6/2010 |

OTHER PUBLICATIONS

Wassmuth, et al., "Cautery-assisted palatal stiffening operation for the treatment of obstructive sleep apnea syndrome," Otolaryngology—Head and Neck Surgery, vol. 123 (1), pp. 55-60 (Jul. 2000).

Teles, et al., "Use of Palatal Lift Prosthesis on Patient Submitted to Maxillectomy: A Case Report," Applied Cancer Research, 2005 vol. 25 (3), pp. 151-154 (2005).

The Pillar Procedure, Restore Medical, Inc., www.restoremedical.com, 2 pp. (2008).

Repose Genioglossus Advancement, Influent Medical, www.influent.com, 1 page (2008).

Cole et al., "Snoring: A Review and a Reassessment", J. of Otolaryngology, pp. 303-306 (1995).

Huang et al., "Biomechanics of snoring", Endeavour, vol. 19(3): pp. 96-100 (1995).

Pang, Kenny et al., "Tongue Suspension Suture in Obstructive Sleep Apnea", Operative Techniques in Otolaryngology, vol. 17, No. 4, Dec. 2006, pp. 252-256.

Schwab et al., "Upper airway and soft tissue changes induced by CPAP in normal subject", Am. J. Respit. Crit. Care Med., vol. 154, No. 4, Oct. 1996, pp. 1106-1116.

Schwartz et al., "Effects of electrical stimulation to the soft palate on snoring and obstructive sleep apnea", J. Prosthetic Dentistry, pp. 273-281 (1986).

Shamsuzzaman et al., "Obstructive Sleep Apnea; Implications for Cardiac and Vascular Disease", JAMA vol. 290 (14); pp. 1906-1914.

The Advance System, Aspire Medical, Inc. www.aspiremedical.com, 3 pp (2008).

Vicente et al., "Tongue-Base Suspension in Conjunction with Uvulopapatopharyngoplasty for Treatement of Severe Obstructive Sleep Apnea: Long-term Follow-Up Results", The Laryngoscope, vol. 115(7), pp. 1223-1227 (2006).

Wiltfang et al., "First results on daytime submandibular electrostimulation of suprahyoidal muscles to prevent night-time hypopharyngeal collapse in obstructive sleep apnea syndrom", Intl J. Of Oral & Maxillofacial Surgery, pp. 21-25 (1999).

Notification of Transmittal of the Internation Search Report and the Written Opinion of the International Search Authority or the Declaration mailed on Mar. 2, 2010; PCT/US2009/051921; International Filing Date: Jul. 28, 2009.

Notification of Transmittal of the Internation Search Report and the Written Opinion of the International Search Authority or the Declaration mailed on May 25, 2010; PCT/US2010/023152; International Filing Date: Feb. 4, 2010.

International Search Report dated Nov. 4, 2009 for International Patent Application No. PCT/US2009/052126.

International Search Report dated Dec. 21, 2009 for International Patent Application No. PCT/US2009/057661.

International Search Report dated Dec. 22, 2009 for International Patent Application No. PCT/US2009/061223.

International Search Report dated Apr. 29, 2010 for International Patent Application No. PCT/US2009/065293.

International Search Report dated May 5, 2010 for International Patent Application No. PCT/US2010/025778.

Schleef et al., Cytokine Activation of Vascular Endothelium, Effects on Tissue-Type 1 Plasminogen Activator Inhibitor; The J. of Biological Chem., vol. 263(12), 1988, pp. 5797-5803.

U.S. Appl. No. 12/182,402 filed Jul. 30, 2008.
U.S. Appl. No. 12/183,955 filed Jul. 31, 2008.
U.S. Appl. No. 12/228,681 filed Aug. 14, 2008.
U.S. Appl. No. 12/238,991 filed Sep. 26, 2008.
U.S. Appl. No. 12/257,563 filed Oct. 24, 2008.
U.S. Appl. No. 12/261,102 filed Oct. 30, 2008.
U.S. Appl. No. 12/378,573 filed Feb. 17, 2009.
U.S. Appl. No. 13/247,713 filed Sep. 28, 2011.
U.S. Appl. No. 13/279,384 filed Oct. 24, 2011.
U.S. Appl. No. 13/314,704 filed Dec. 8, 2011.

* cited by examiner

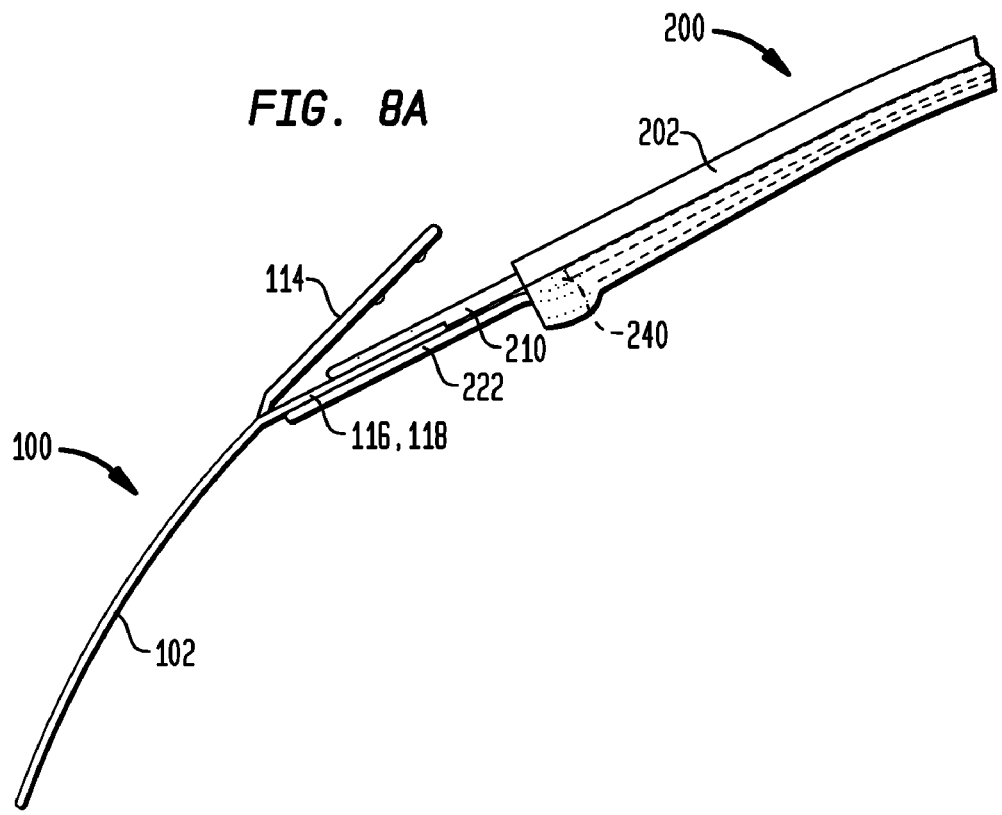
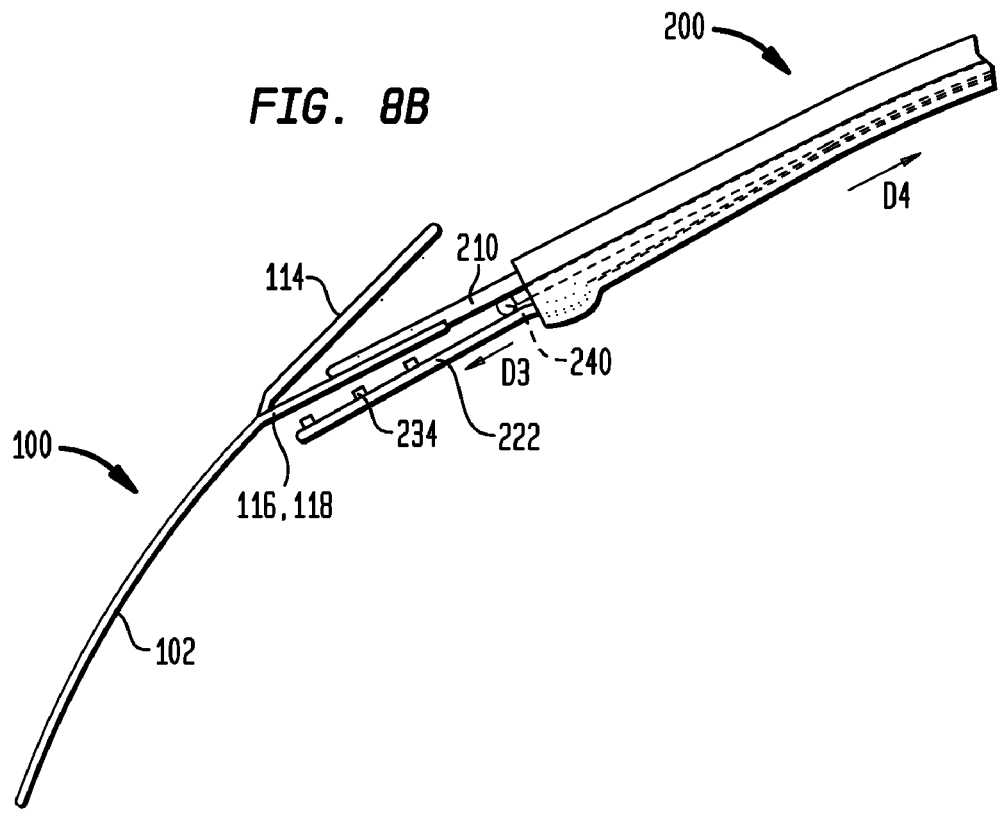

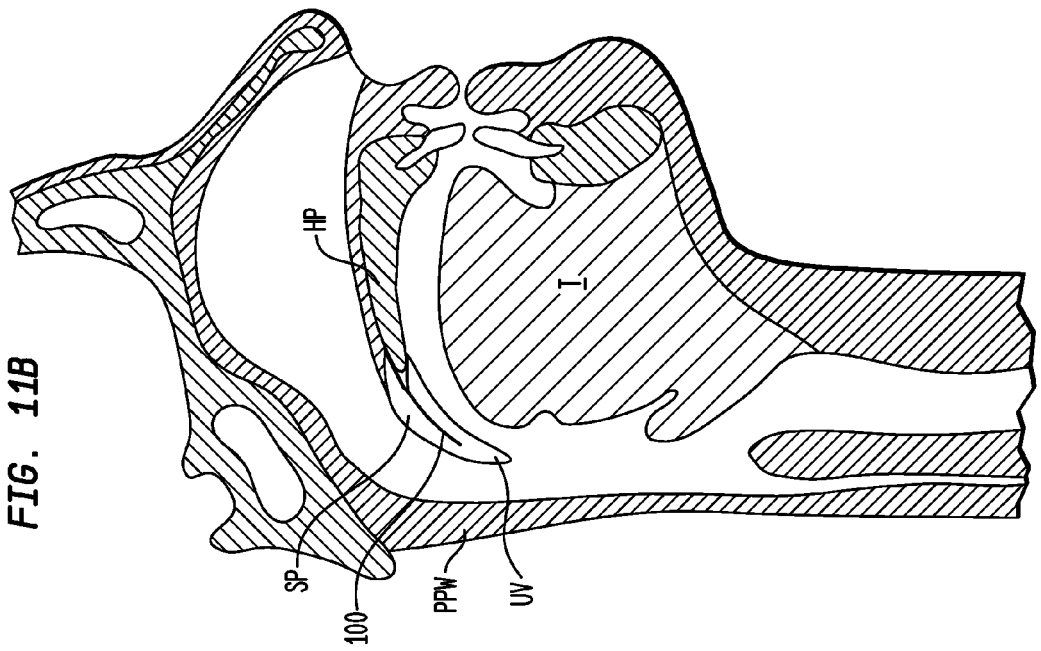
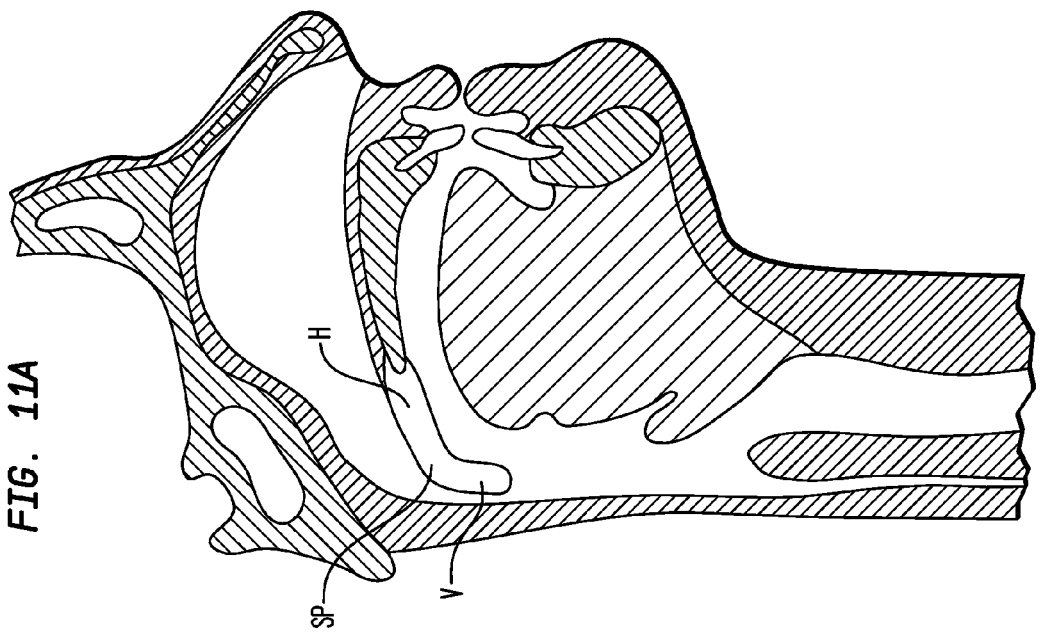

IMPLANT SYSTEMS AND METHODS FOR TREATING OBSTRUCTIVE SLEEP APNEA

BACKGROUND OF THE INVENTION

1. Field of the Invention

The present invention generally relates to treating sleep disorders, and more specifically relates to implant systems, devices and methods for treating patients suffering from obstructive sleep apnea.

2. Description of the Related Art

Obstructive sleep apnea (OSA) is caused by a blockage of the airway, which usually occurs when the soft tissue in the throat collapses and closes during sleep. The blockage can occur in a portion of the pharyngeal lumen and may include obstructions formed by the collapse of the tongue against the posterior wall of the pharynx, the collapse of the lateral pharyngeal walls, and the combined collapse of the tongue with impingement of the soft palate, particularly the posterior portion of the soft palate including the uvula. During each apnea event, the brain briefly arouses the sufferer in order to initiate the resumption of breathing. This type of sleep, however, is extremely fragmented and of poor quality.

According to the National Institutes of Health, OSA affects more than twelve million Americans. When left untreated, OSA may result in high blood pressure, cardiovascular disease, weight gain, impotency, headaches, memory problems, job impairment, and/or motor vehicle crashes. Despite the seriousness of OSA, a general lack of awareness among the public and healthcare professionals results in the vast majority of OSA sufferers remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a strict regimen of use, subject the patient to discomfort during sleep, and result in repeated arousal of the patient.

Another treatment, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal for stiffening the flaccid palate.

Surgical procedures such as those mentioned above continue to have problems. Specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Another surgical procedure for treating OSA uses several braided PET cylinders that are implanted in tissue to make the tissues of the tongue or uvula more rigid and less prone to deflection. The Pillar™ Palatal Implant System sold by Restore Medical of St. Paul, Minn. consists of cylindrical-shaped elements of braided polyester filaments that are implanted in the soft palate for reducing the incidence of airway obstructions in patients suffering from mild to moderate OSA. Use of the Pillar device may result in adverse side effects, including extrusion of the cylindrical-shaped elements, infection, and patient discomfort.

Another implant system, sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, however, the suture component of this device may act as a "cheese cutter" to the tongue, causing device failure and requiring subsequent removal.

Another effort for treating OSA involves creating an auxiliary airway for bypassing the clogged portion of the main airway. In one embodiment of commonly assigned U.S. patent application Ser. No. 12/182,402, filed Jul. 30, 2008, the disclosure of which is hereby incorporated by reference herein, an auxiliary airway is formed by implanting an elongated conduit beneath a pharyngeal wall of the pharynx. The elongated conduit has a proximal end in communication with a first region of the pharynx, a distal end in communication with a second region of the pharynx, and an intermediate section extending beneath the pharyngeal wall for bypassing an oropharynx region of the pharynx.

Magnets have also been used for treating OSA. For example, in one embodiment of commonly assigned U.S. patent application Ser. No. 12/183,955, filed Jul. 31, 2008, the disclosure of which is hereby incorporated by reference herein, a magnetic implant includes a bone anchor, a first magnet coupled to the bone anchor, a tongue anchor, a second magnet coupled to the tongue anchor, and a support for aligning the first and second magnets so that a repelling force is generated between the magnets for urging the second magnet away from the first magnet and toward the bone anchor. The support maintains the first magnet at a fixed distance from the bone anchor, aligns the first magnet with the second magnet, and guides movement of the first and second magnets. The magnetic implant disclosed in one or more embodiments of the '955 application does not have a hard stop so as to avoid the "cheese-cutter" effect observed when using implants having a hard stop.

In spite of the above advances, there remains a need for additional systems, devices and methods for treating OSA through minimally invasive approaches that provide long term results, that encourage patient compliance, and that minimize patient discomfort.

SUMMARY OF THE INVENTION

In one embodiment, the present invention provides a medical implant for the treatment of obstructive sleep apnea including an implant device, such as an elastic extension member, affixed to the distal end of the hard palate and extending into the uvula. The implant device is adapted to provide a degree of support that is sufficient to resist distal movement of the tongue when the tongue is relaxed and the patient is in a supine position, but not so great as to impair the soft palate and the uvula from sealing the nasal cavity during the act of swallowing. In one embodiment, two or more implant devices are implanted in the soft palate, and the proximal ends of at least two of the devices are connected with the hard palate.

In one embodiment, a system for treating obstructive sleep apnea includes a body implantable in a soft palate, and a fastening element at a proximal end of the body for connecting the body with a hard palate. In one embodiment, the body is curved and has a convex top surface and a concave bottom surface. The radius of the curve and the size of the body may vary depending upon the needs of the patient. When implanted, the convex top surface of the body preferably faces toward an upper end of a patient and the concave bottom surface of the body preferably faces toward the lower end of the patient. In one embodiment, the implant extends to the uvula for changing the shape of the uvula and/or providing support for the uvula.

In one embodiment, the fastening element at the proximal end of the body is engageable with the hard palate for securing the body to the hard palate. In one embodiment, the fastening element desirably includes at least one barb adapted to engage the hard palate for anchoring the body to the hard palate. In one embodiment, the fastening element includes at least one tab projecting from the proximal end of the body and at least one barb projecting from the at least one tab. In one embodiment, an implantable body includes an upper tab, and a pair of opposing lower tabs that are normally biased toward one another. The opposing tabs preferably include inwardly projecting barbs that oppose one another. Upon implantation, the upper tab preferably overlies a top surface of the hard palate and the pair of lower tabs preferably underlie a bottom surface of the hard palate. The tabs bias toward one another so that the barbs on the respective tabs bite into the bone of the hard palate for securing the implant to the hard palate.

In one embodiment, the body has a surface adapted to promote tissue in-growth. The tissue in-growth promoting surface is desirably selected from a group of outer surfaces including a textured surface, a porous surface, a braided surface, a mesh surface, a fleece surface, and a coating for inducing bone or tissue in-growth. In one embodiment, the body is made of materials such as nitinol, stainless steel, biocompatible polymers, temperature-sensitive materials, and/or shape memory materials.

In one embodiment, an implant for supporting a uvula for treating obstructive sleep apnea includes a body implantable in a soft palate, the body having a distal end and a proximal end, and a fastening element adjacent the proximal end of the body for fastening the body to a hard palate. In one embodiment, the fastening element desirably includes at least one anchoring tab adapted to overlie the surface of a hard palate, the at least one anchoring tab having at least one barb. In one embodiment, the fastening element may include fasteners such as barbs, bone anchors, screws, tacks, pins, wire, sutures, staples, rods, and/or adhesive.

In one embodiment, a method of treating obstructive sleep apnea includes forming a surgical opening in a soft palate, inserting an implant device through the surgical opening and into the soft palate, and securing the implant device to a hard palate. A distal end of the implanted device desirably engages the uvula for supporting and/or changing the shape of the uvula. In one embodiment, the shape of the soft palate is changed by the implant as the implant device is inserted into the soft palate. The method may include using a fastening element for securing the implant to the hard palate. The implant may include a body, and the fastening element for securing the body to the hard palate. The body may be curved, and the soft palate may be curved by the curved body during the inserting step. The fastening element preferably includes opposing tabs projecting from the proximal end thereof, whereby the opposing tabs are normally biased toward one another. In one embodiment, the opposing tabs include tissue engaging barbs. In one embodiment, the implant device may be implanted directly within the oral cavity of a patient. In one embodiment, the implant device may be implanted through the nasal passageway.

In one embodiment, the implant devices disclosed herein may be used to re-shape the soft palate for minimizing the likelihood of obstructive sleep apnea episodes associated with long, flat soft palates and/or L-shaped soft palates. In one embodiment, when a long, flat soft palate is causing OSA, an implant having a curved body may be implanted into the soft palate for increasing the curve of the soft palate. In another embodiment, when an L-shaped soft palate is causing OSA, an implant may be inserted for reducing the curve or angle of the soft palate. Thus, in one embodiment, a plurality of implants having varying radii may be provided, whereby an implant having a desired amount of curve may be utilized for increasing or reducing the curve of the soft palate (i.e. changing the shape of the soft palate). In one embodiment, a plurality of implants having varying sizes may be provided so as to enable medical personnel to select an implant having a desired size.

In one embodiment, the implant device is made of a shape changeable material such as nitinol. The nitinol may have a super elastic property and/or a shape memory property. In the one embodiment whereby the nitinol has a shape memory property, the nitinol material has a first transition temperature set just above body temperature, whereby the nitinol transitions into a pre-determined elastic configuration to support the uvula and thereby keep the airway open. In this state, the implant may be useful during sleep. The implant desirably includes a second lower transition temperature set somewhat below body temperature, whereby the implant transitions into a ductile state allowing the uvula move in a posterior direction. This state or condition may be suitable for when the patient is awake, whereupon there is no need for the implant to urge the uvula into a more anterior position. An implant having shape memory properties may be used in other areas of the airway. In one embodiment, a transition into the ductile state may be initiated by gargling with cold water. In one embodiment, a transition into a pre-determined elastic state may be achieved by drinking warm or hot fluid.

In one embodiment, an implant device made of a shape memory material, such as nitinol, may be implanted when at a temperature that is below body temperature. When below the normal body temperature, the material is easily shapeable. After implantation, the material may be elevated to body temperature, whereby the implant assumes its pre-determined shape to support the uvula. In certain preferred embodiments, the implant device is made of stainless steel, such as 300 and 400 series stainless steel. The implant device may also be made of a biocompatible polymer.

In one embodiment, the degree of support provided by the implant may be customized by adjusting the length of the implant, such as by trimming the implant. The cross-sectional geometry of the implant may also be changed to reduce or increase the section modulus.

The outer surface of the implant device may be modified to encourage tissue in-growth so as to stabilize the implant within tissue and minimize opportunity for tissue erosion. Modification of the outer surface to promote tissue in-growth may be achieved by texturizing the outer surface, making the implant porous through the addition of openings or apertures, encapsulating the implant with a braided structure, surgical mesh, or fleece type material, and/or at least partially coating the implant with bone growth stimulating agents such as hydroxyapatite.

Although the present is not limited by any particular theory of operation, it is believed that providing an implant device that supports the uvula and that is connected to the distal end of the hard palate provides more positive positioning of the uvula and enables the uvula to provide greater resistance to distal tongue movement than implants that are not supported by the hard palate. The implant also provides a balanced level of uvula support which provides tongue support when needed, but does not inhibit swallowing. The shape changing feature preferably allows greater uvula support (and thereby tongue support) during times of rest, and less support during waking hours. The modification of the outer surface of the implant preferably reduces the chance of tissue erosion and provides greater lateral stability to the implant. The ability to implant the device through the nasal passageway results in an implant being more cranial and thereby minimizing the tongue's sensitivity to the implants' presence. Furthermore, the implant device disclosed herein provides a medical procedure that does not damage the musculature within the soft palate and maintains all mucosal surfaces, which enables the natural musculature to continue providing support in addition to that provided by the implant.

These and other preferred embodiments of the present invention will be described in more detail below.

BRIEF DESCRIPTION OF THE DRAWING

FIG. 8A shows a cross-sectional view of the implant insertion tool of FIGS. 7A-7D with the insertion tool in a first position, in accordance with on embodiment of the present invention.

FIG. 8B shows a cross-sectional view of the implant insertion tool of FIGS. 7A-7D with the insertion tool in a second position, in accordance with one embodiment of the present invention.

FIGS. 10A-1, 10B-1 and 10C-1 show a magnified view of the insertion method shown in FIGS. 10A-10C.

FIGS. 11A and 11B show a method of treating obstructive sleep apnea, in accordance with one embodiment of the invention.

DETAILED DESCRIPTION

Figure 1:
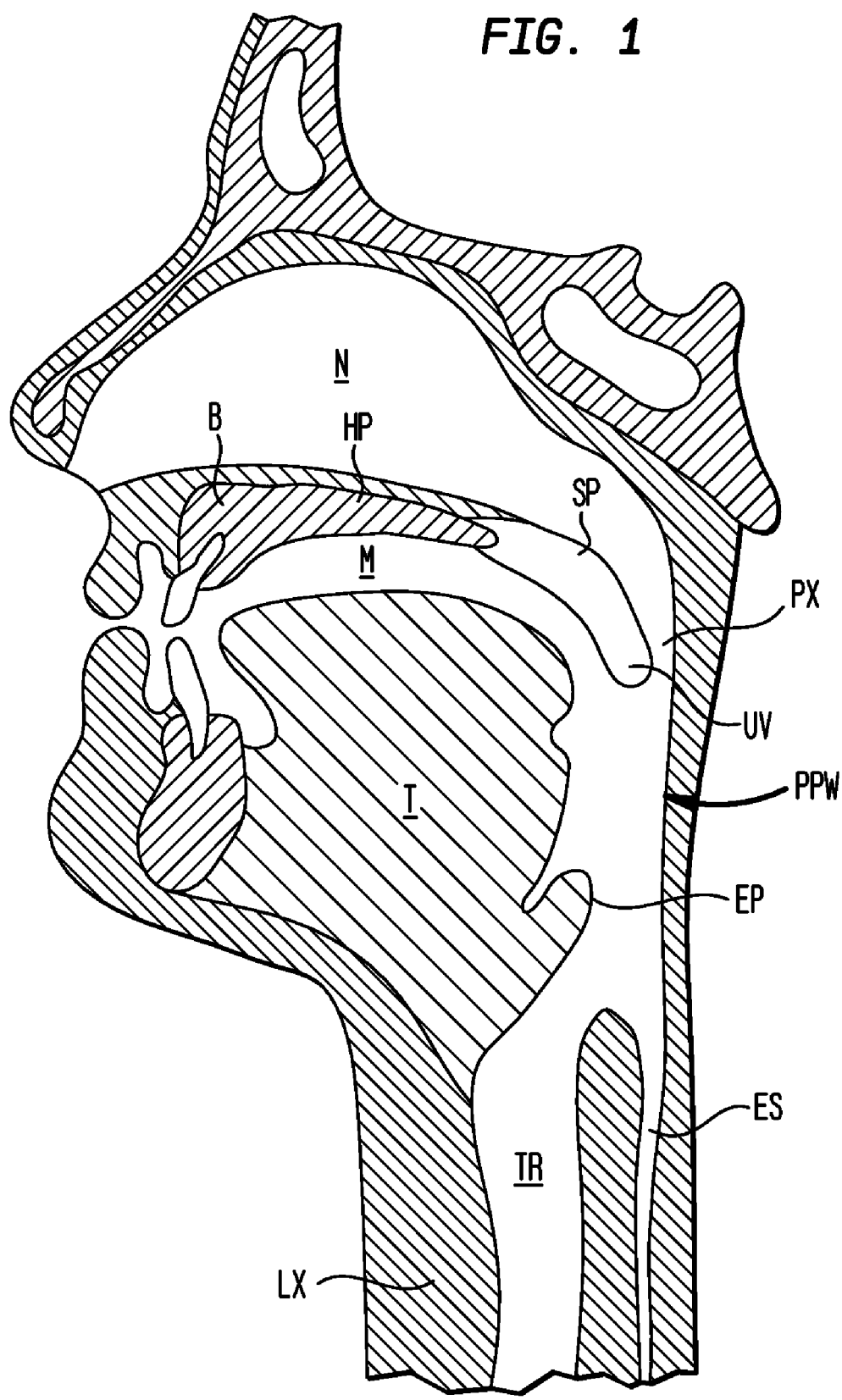
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP including the uvula UV at the posterior end thereof, the mouth M, the tongue T, the trachea TR, the epiglottis EP, the esophagus ES, and the posterior pharyngeal wall PPW.

Figure 2:
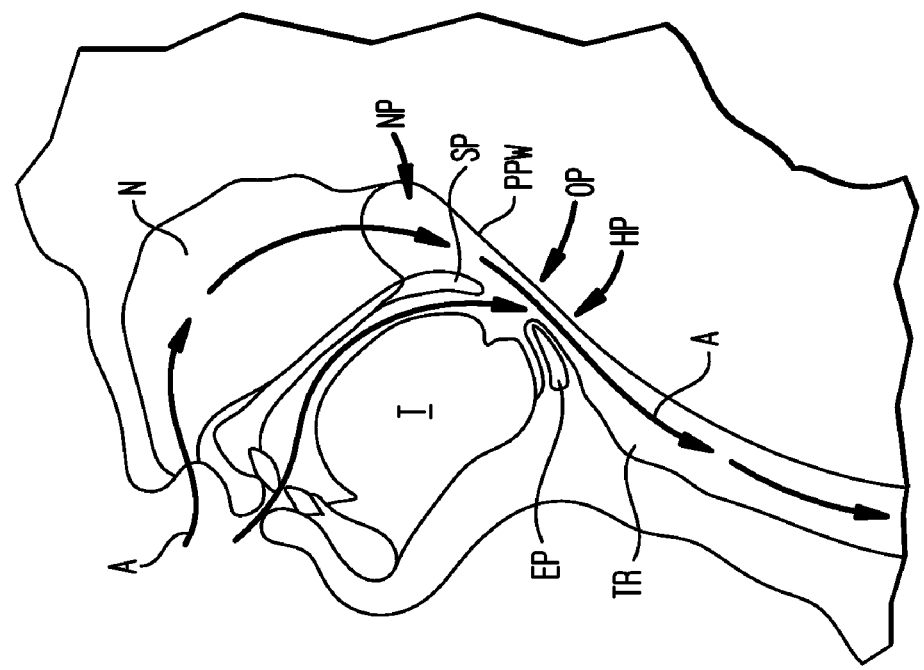
FIG. 2 shows a cross-sectional view of the nasal cavity and the pharynx of a human during normal breathing.

In a human body, an air filled space between the nasal cavity N and the larynx LX is referred to as the upper airway. The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than is necessary and extends a significant distance between the back of the tongue T and the posterior pharyngeal wall PPW. The midline posterior end of the soft palate is referred to as the uvula, which is the soft tissue that extends downward from the soft palate over the back of the tongue.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent, which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible.

Figure 3:
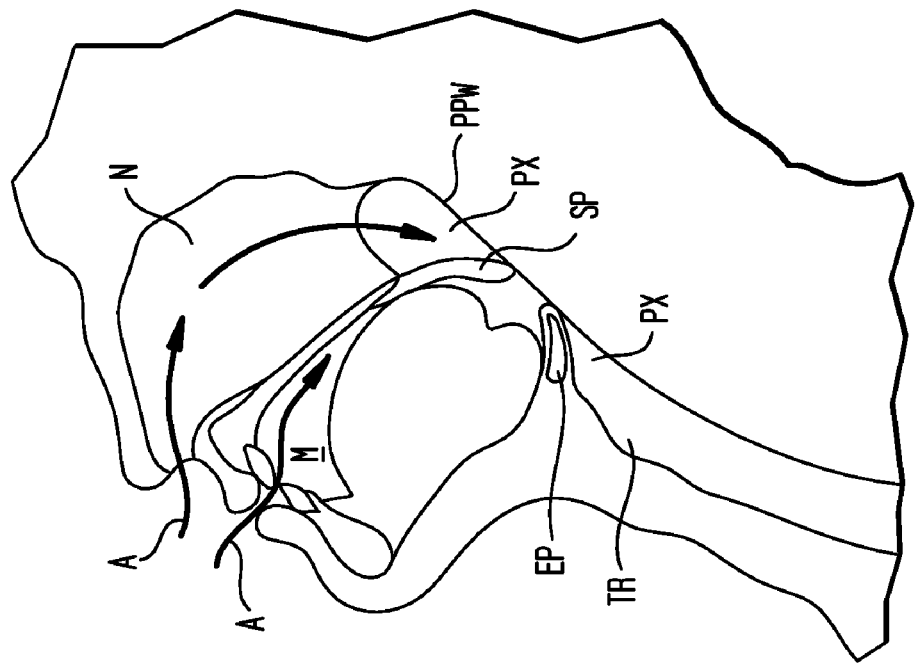
FIG. 3 shows a cross-sectional view of the nasal cavity and the pharynx of a human during an obstructive sleep apnea episode.

Referring to FIG. 3, without normal muscle tone to keep their shape and to keep them in place either alone or as a group, the posterior surface of the tongue T, the epiglottis EP, and the soft palate SP tend to easily collapse to block the airway A.

Figure 4:
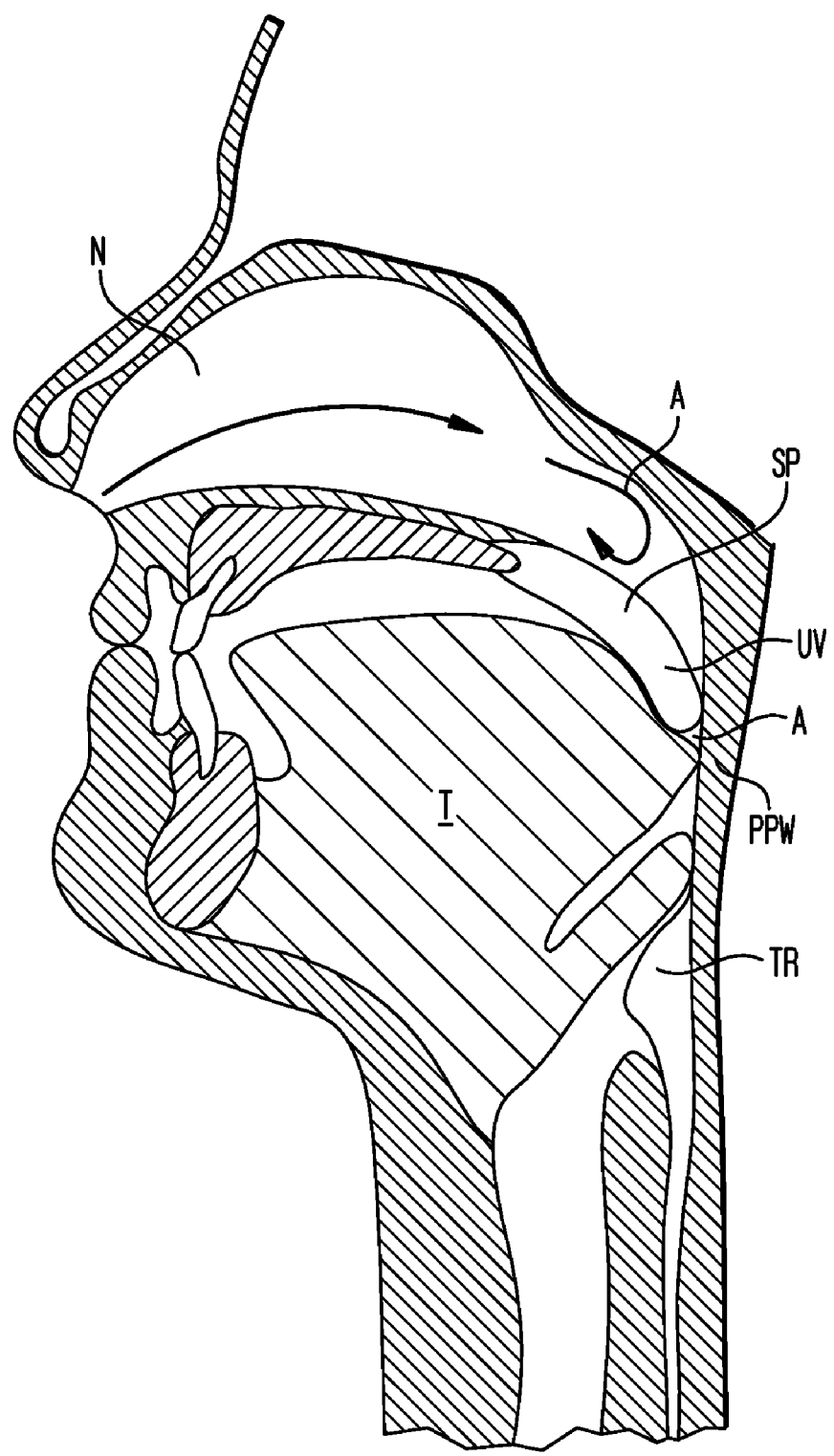
FIG. 4 shows another cross-sectional view of the nasal cavity and the pharynx of a human during an obstructive sleep apnea episode.

Referring to FIG. 4, during sleep, the proximal end of the tongue T may block the airway A between the nasal passages N and the upper end of the trachea TR. The soft palate SP may also relax and have the uvula UV slide between the back of the tongue T and the posterior pharyngeal wall PPW. In one embodiment, the present invention provides an implant that changes the shape of the soft palate so that it does not move into the position shown in FIG. 4. The implant also desirably provides support to the tongue T so that it does not sag in a posterior direction against the posterior pharyngeal wall, as shown in FIG. 4.

Referring to FIGS. 5A-5E, in one embodiment, an implant 100, such as a soft palate implant, includes a main body 102 that is implantable in a soft palate. The main body 102 has a posterior or distal end 104, and an anterior or proximal end 106 that is adapted to be coupled and/or secured to a hard palate of a patient. The main body 106 of the implant 102 preferably includes a top surface 108 and a bottom surface 110. The main body 102 of the implant 100 preferably has a length L and a width W that may vary depending upon patient anatomy. The main body 102 and the top and bottom surfaces 108, 110 may be curved. The curvature of the main body 102 may vary depending upon patient anatomy, the specific problem affecting the patient and/or surgical requirements. In one embodiment, the curvature of the main body 102 may be varied as required to prevent the back of a patient's tongue from pressing against the posterior pharyngeal wall.

Referring to FIGS. 5A-5E, in one embodiment, the proximal end 106 of the soft palate implant 102 includes a securing element 112 for securing the implant to a hard palate of a patient. In one embodiment, the securing element includes an upper anchoring tab 114 adapted to engage an upper surface of a hard palate, and a pair of lower anchoring tabs 116, 118 adapted to engage a lower surface of a hard palate.

Figure 5A:
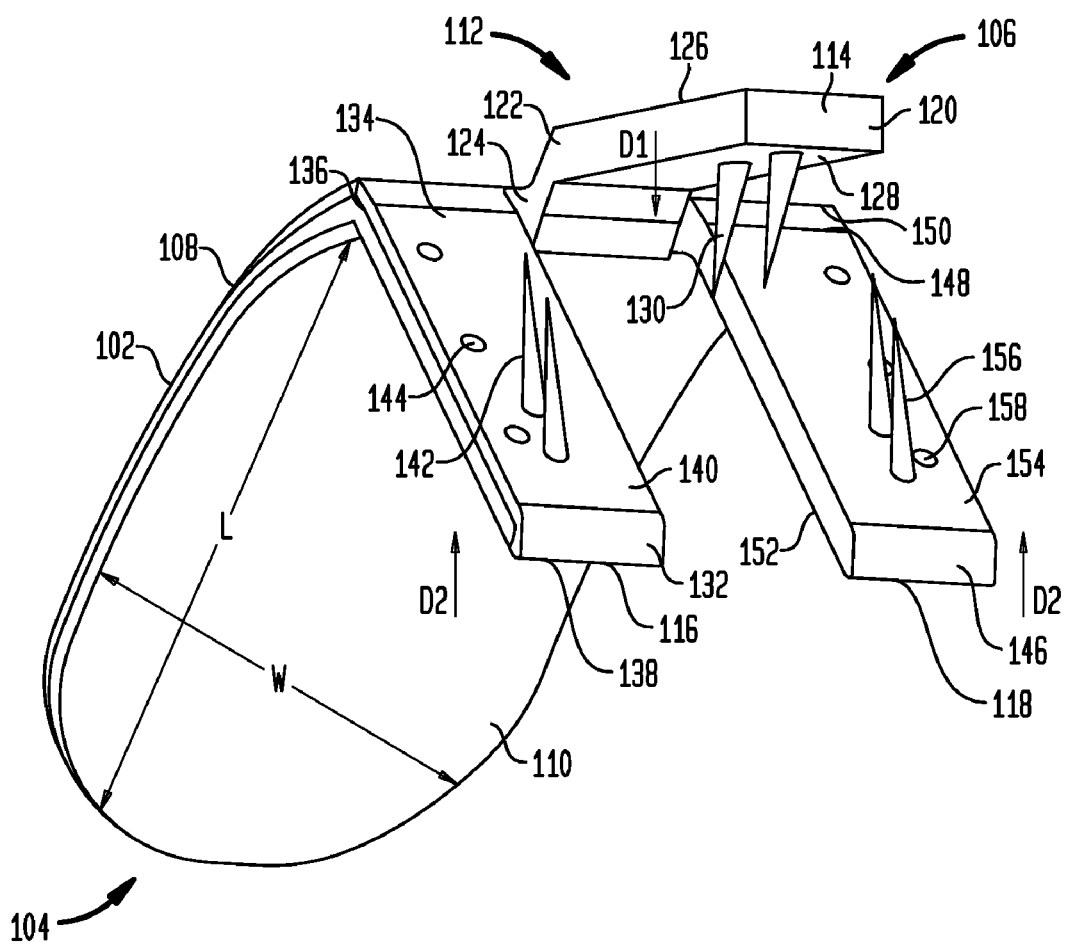
FIGS. 5A-5E show a perspective view of an implant used for treating obstructive sleep apnea, in accordance with one embodiment of the present invention.
Figure 5B:
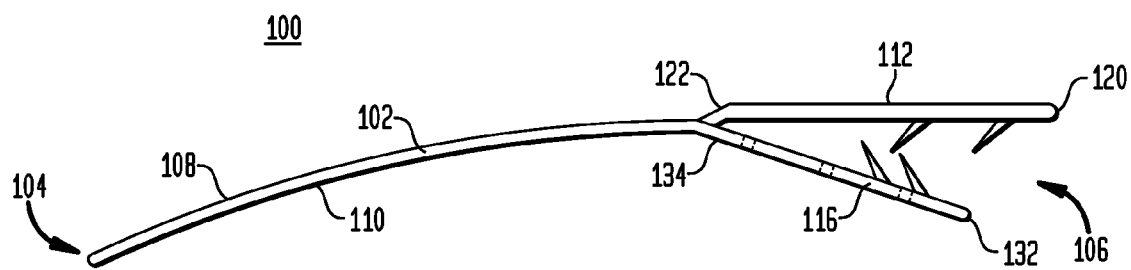
Figure 5C:
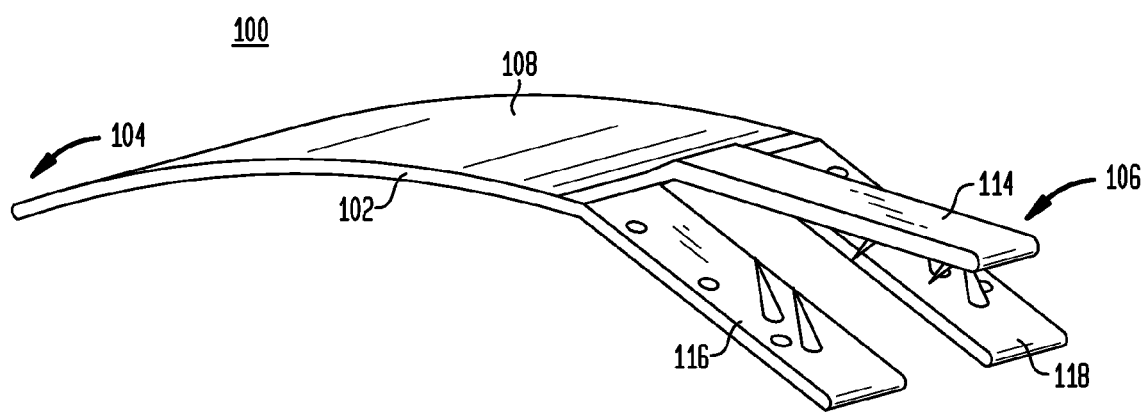
Figure 5D:
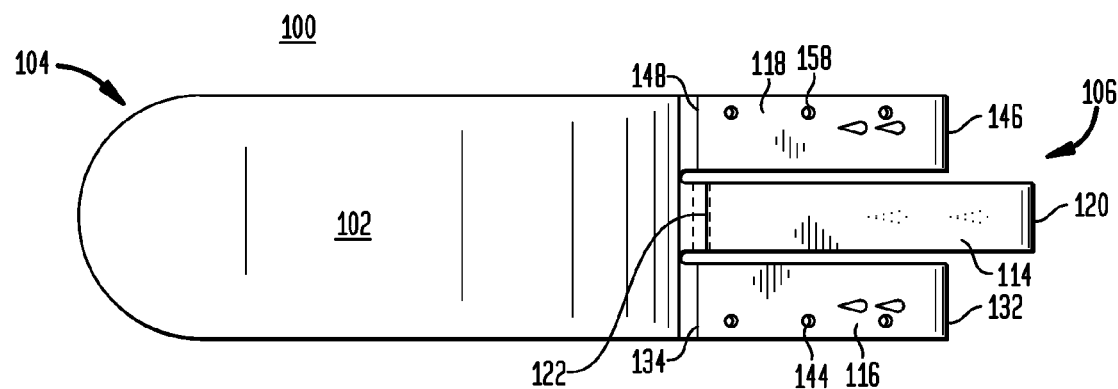
Figure 5E:
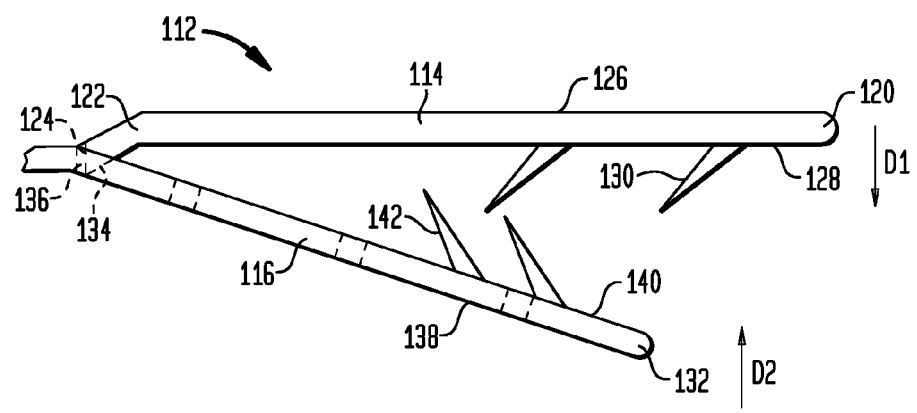

Referring to FIGS. 5A and 5E, in one embodiment, the upper anchoring tab 114 desirably includes a leading end 120 and trailing end 122 that is connected to the main body 102 via a flexible connection 124. The upper anchoring tab 114 includes an outer face 126 and an inner face 128 having anchoring barbs 130. The anchoring barbs 130 are adapted to bite into an upper surface of a hard palate for anchoring the proximal end 106 of the soft palate implant 100 to the hard palate. The flexible connection 124 normally biases the upper anchoring tab 114 toward the opposing lower anchoring tabs 116,118 in a downward direction designated $D_1$.

The lower anchoring tabs include the first lower tab 116 having a leading end 132 and a trailing end 134 that is connected with the main body 102 via a flexible connection 136. The flexible connection 136 normally biases the first lower tab 116 toward the upper tab 114 in an upward direction designated $D_2$. The first lower tab 116 includes an outer surface 138 and an inner surface 140 having anchoring barbs 142 projecting therefrom. In one embodiment, the anchoring barbs 142 are adapted to bite into an underside surface of a hard palate. The first lower tab 116 also desirably includes through holes 144 that extend from the inner surface 140 toward the outer surface 138. In one embodiment, the through holes 144 extend completely between the inner and outer surfaces 140, 138. In one embodiment, the through holes 144 are blind detents that extend only part of the way between the inner surface and the outer surface.

The second lower tab 118 preferably includes a leading end 146 and a trailing end 148 that is coupled with a proximal end of the main body via a flexible connection 150. The flexible connection 150 normally biases the second lower tab 118 toward the upper anchoring tab 114 in an upward direction designated $D_2$. The second lower anchoring tab 118 includes an outer surface 152 and an inner surface 154 having bone anchoring barbs 156 projecting therefrom. The bone anchoring barbs 156 are preferably adapted to bite into an underside surface of a hard palate. The second lower anchoring tab 118 also includes through holes 158 adapted to receive posts at a distal end of an insertion tool as will be described in more detail below.

Figure 6:
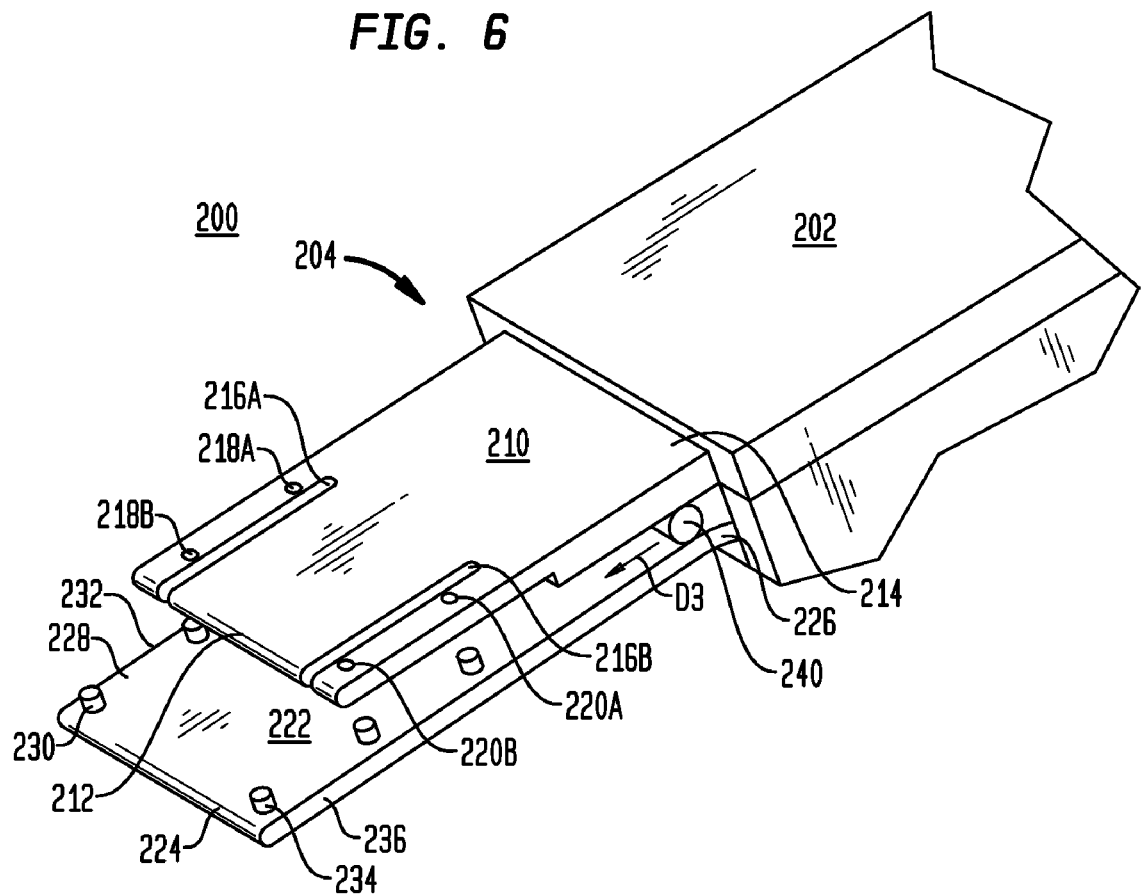
FIG. 6 shows a distal end of an insertion tool for inserting the implant shown in FIGS. 5A-5E, in accordance with one embodiment of the present invention.

Referring to FIG. 6, in one embodiment, an insertion tool 200 for implanting the implant 100 shown in FIGS. 5A-5E includes a shaft 202 having a distal end 204 that secures and deploys the implant. The distal end 204 of the insertion tool 200 desirably includes an upper blade 210 having a leading end 212 and a trailing end 214. The upper blade 210 includes a pair of aligned slits 216A, 216B that extend from the leading end 212 toward the trailing end 214. The upper blade 210 includes a first set of through holes 218A, 218B adjacent the first slot 216A, and a second set of through holes 220A, 220B adjacent the second slot 216B.

Referring to FIG. 6, in one embodiment, the insertion tool 200 also preferably includes a lower blade 222 having a leading end 224 and a trailing end 226. The lower blade 222 includes an inner surface 228 having a first set of lower anchoring tab securing posts 230 aligned with one another and extending along a first lateral edge 232 of the lower blade 222 and a second set of lower anchoring tab securing posts 234 aligned with one another and extending along a second lateral edge 236 of the lower blade 222. In one embodiment, the aligned securing posts 230, 234 on the lower blade 222 may be aligned with the through holes 218, 220 extending through the upper blade 212.

In one embodiment, the lower blade 222 is adapted to be wedged away from the upper blade 210 for releasing the uvula implant from the distal end 204 of the insertion tool. In one embodiment, the insertion tool 200 includes a push bar 240 that is coupled with an actuator (not shown) located at a proximal end of the insertion tool. Upon activation of the actuator (not shown), the push bar 240 preferably moves in a distal direction designated $D_3$ for wedging the leading end 224 of the lower blade 222 away from the upper blade 210. In one embodiment, the push bar may wedge the upper blade away from the lower blade.

Figure 7A:
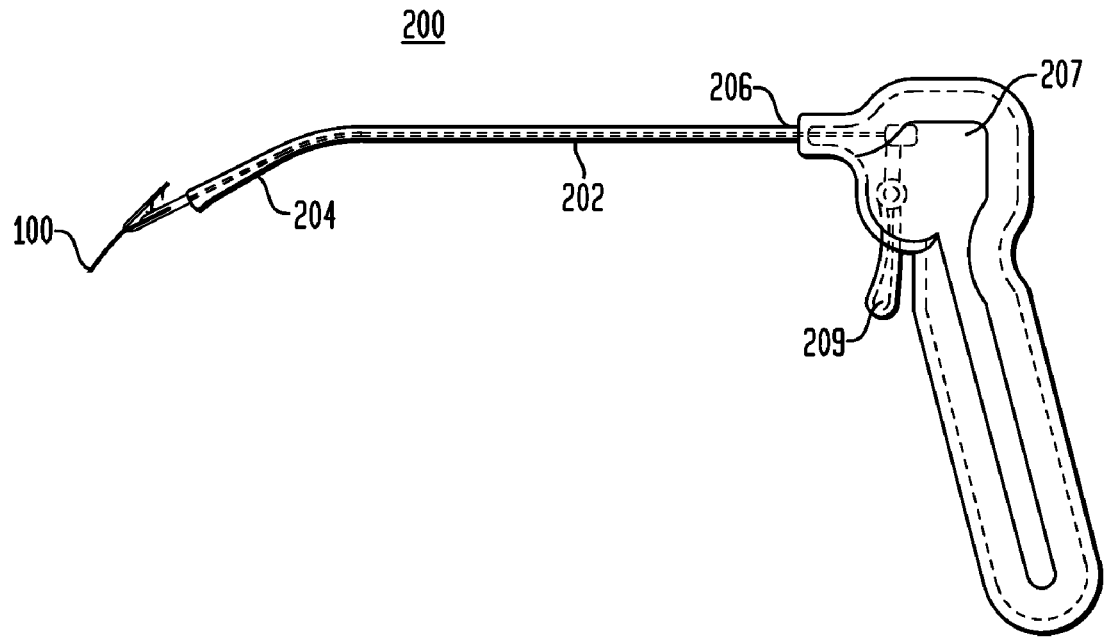
FIGS. 7A-7D show the implant of FIGS. 5A-5E secured to the distal end of the insertion tool of FIG. 6, in accordance with one embodiment of the present invention.
Figure 7B:
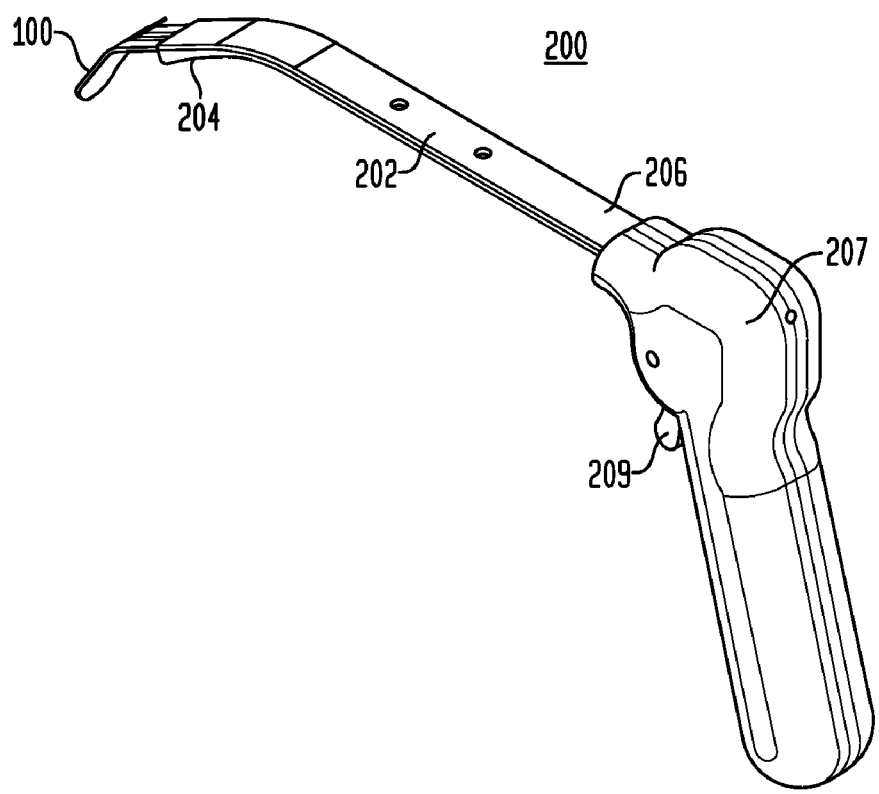
Figure 7C:
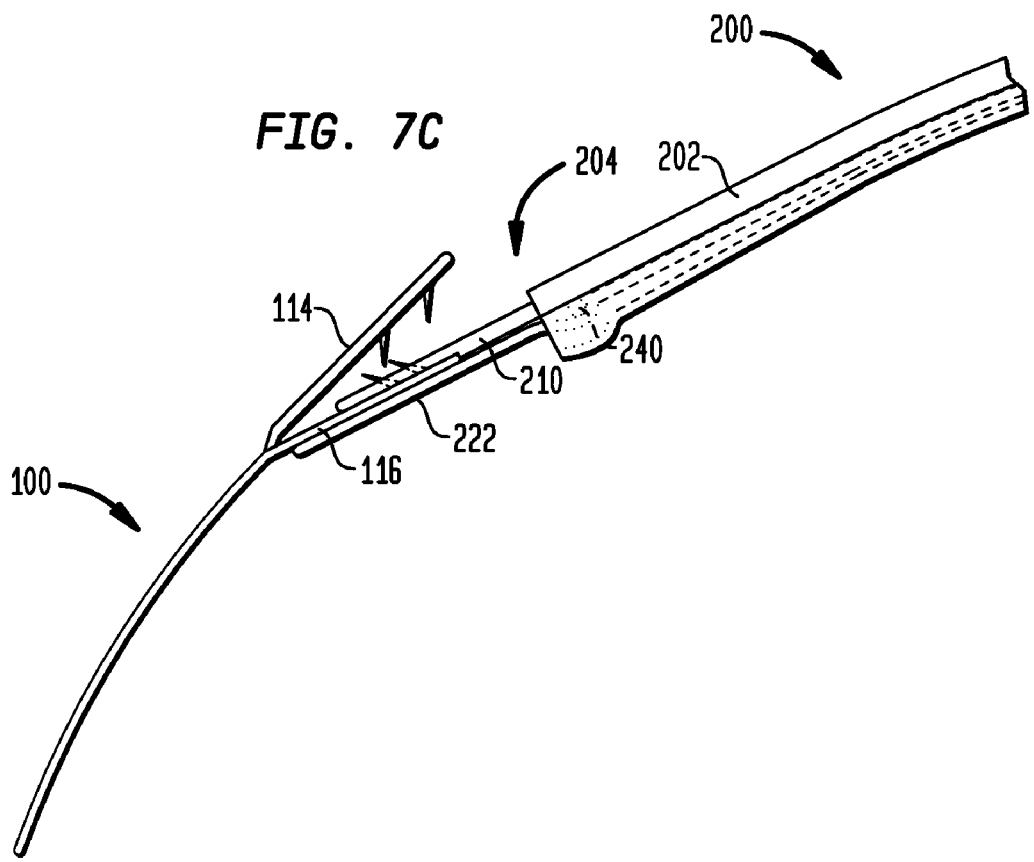
Figure 7D:
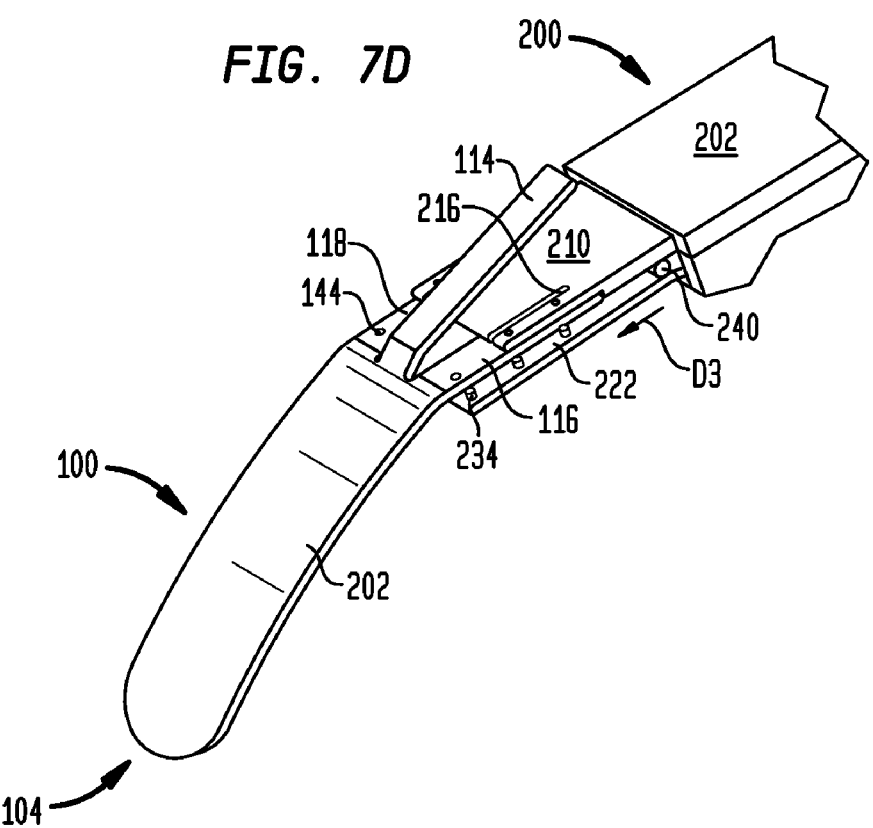

Referring to FIGS. 7A-7D, in one embodiment, the soft palate implant 100 is preferably securable to the distal end 204 of the insertion tool 200. Referring to FIGS. 7A-7D, in one embodiment, the insertion tool 200 includes an elongated shaft 202 having a distal end 204 and a proximal end 206 coupled with a housing 207 having an actuator or trigger 209. Referring to FIGS. 7C and 7D, in one embodiment, the lower anchoring tabs 116, 118 are held between the upper blade 210 and the lower blade 222, with the barbs 142 projecting from the inner surfaces of the lower tabs 116, 118 passing through the slots 216 adjacent the lateral edges of the upper blade 210. In one embodiment, the upper and lower blades 220, 222 pinch towards one another for holding the lower anchoring tabs 116, 118 therebetween. The securing posts 234 on the lower blade 222 preferably pass through the through holes 144, 158 of the lower anchoring tabs 116, 118 for more securely holding the implant to the distal end 204 of the insertion tool 200.

Referring to FIGS. 7C and 7D, in one embodiment, when the lower anchoring tabs 116, 118 are held between the upper and lower blades 210, 224, the upper anchoring tab 114 preferably lies above the upper blade 210. In one embodiment, during an insertion operation, the insertion tool 200 secures the implant 100 so that the distal end 104 of the implant 100 may be guided into a surgical opening, such as an incision formed in the soft palate of a patient. In one embodiment, the push bar 240 is actuated so that it moves in the direction $D_3$ toward the distal end of the insertion tool 200. As the push bar 240 moves toward the distal end, the upper and lower blades 210, 222 are wedged away from one another for releasing the lower anchoring tabs 116, 118 from the insertion tool. In one embodiment, the respective upper and lower anchoring tabs will preferably bias toward one another, whereby the barbs on the inner surfaces of the tabs bite into the respective upper and lower faces of the hard palate for anchoring the implant 100 to the hard palate.

Referring to FIGS. 8A and 8B, in one embodiment, the distal end of the insertion tool 200 is adapted to secure a proximal end of the implant device 100. The distal end of the insertion tool preferably releases the implant device after the device has been implanted in tissue. In one preferred embodiment, the insertion tool is used to implant the implant device in the soft palate of a patient and anchor a proximal end of the implant device to the patient's hard palate.

Referring to FIG. 8A, in one embodiment, the upper and lower blades pinch the pair of lower tabs 116, 118 therebetween, and the push bar 240 is in a retracted position. In FIG. 8B, the push bar 240 is advanced in a distal direction designated $D_3$ for wedging the lower blade 222 away from the upper blade 210 so as to release the pair of lower tabs 116, 118 from the distal end of the insertion tool 200. The insertion tool may then be retracted in the direction designated $D_4$ so as to release the implant device 100 and leave the proximal end of the implant device anchored to a structure, such as the hard palate of a patient.

Figure 9A:
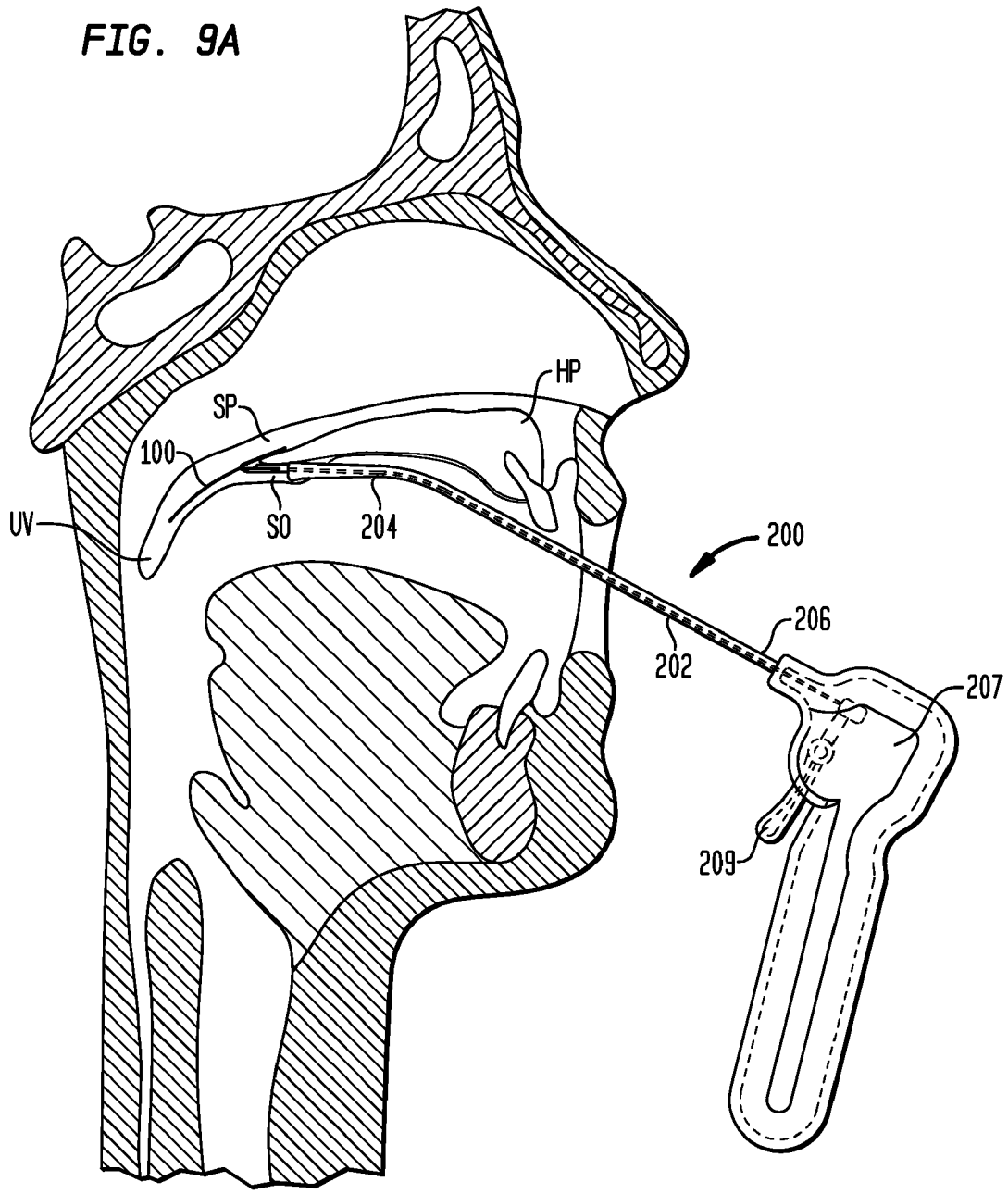
FIG. 9A shows a method of inserting the implant of FIGS. 5A-5D in a patient using the insertion tool shown in FIGS. 6 and 7A-7D, in accordance with one embodiment of the present invention.
Figure 9B:
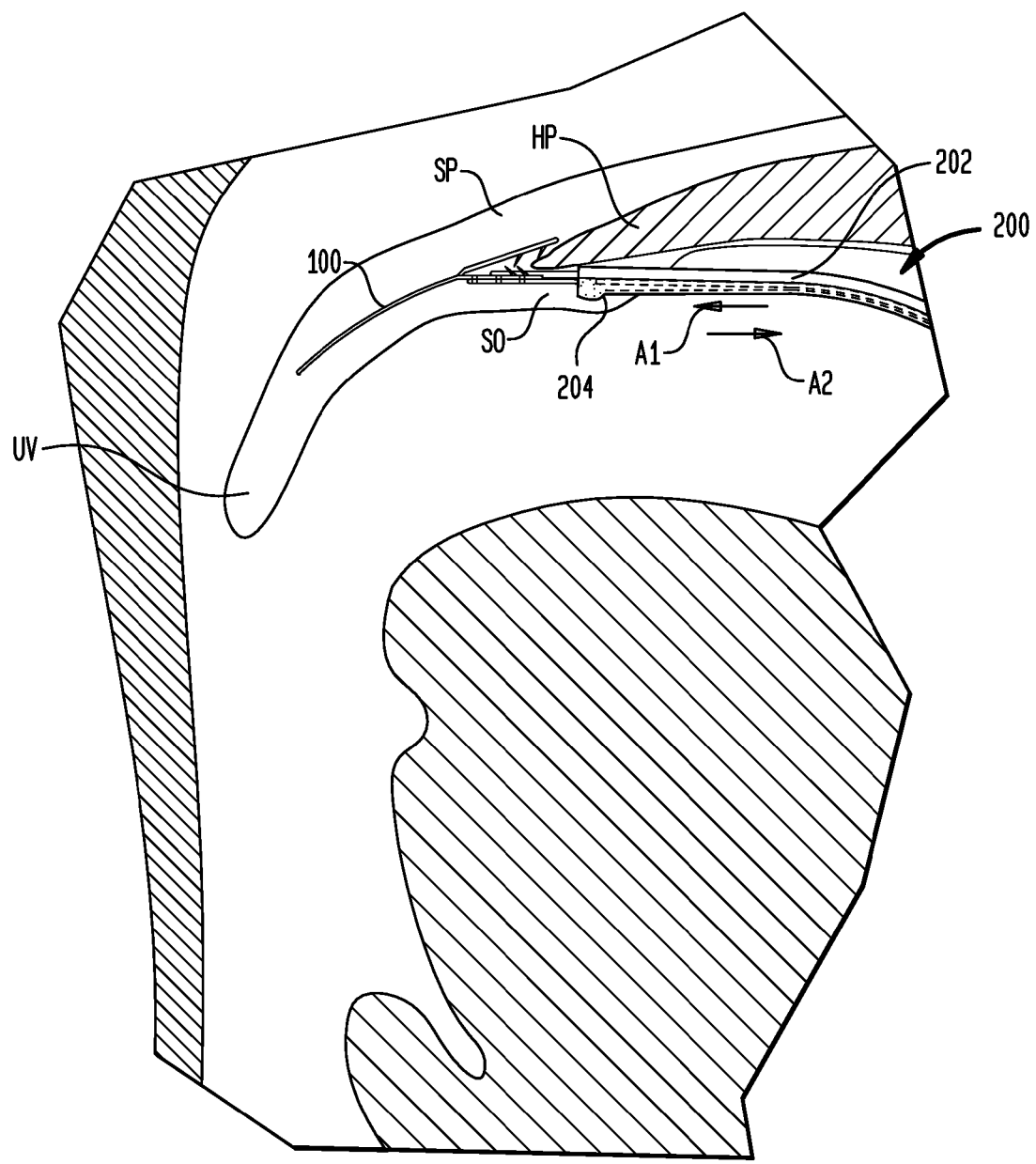
FIG. 9B shows a magnified view of the implant and the distal end of the insertion tool shown in FIG. 9A.

Referring to FIG. 9A, in one embodiment, a surgical opening SO is formed in the soft palate SP and an implant device 100 is inserted into the surgical opening for supporting the soft palate SP and the uvula UV. In one embodiment, the implant 100 is preferably held by the upper and lower blades at the distal end 204 of the insertion tool 200. FIG. 9B shows a magnified view of the distal end 204 of the insertion tool 200 with the implant 100 inserted into the surgical opening SO in the soft palate SP. In one embodiment, the shaft 202 of the insertion tool 200 is moved in the direction $A_1$ for inserting the implant 100 into the surgical opening SO. The shaft 202 of the insertion tool 200 is then retracted in the direction $A_2$ so that the upper tab 114 overlies the top surface of the hard palate HP and the lower tabs 116, 118 underlie the bottom surface of the hard palate. The push bar is then advanced to open the upper and lower blades of the tool for releasing the implant 100 from the distal end of the insertion tool.

Figure 10A:
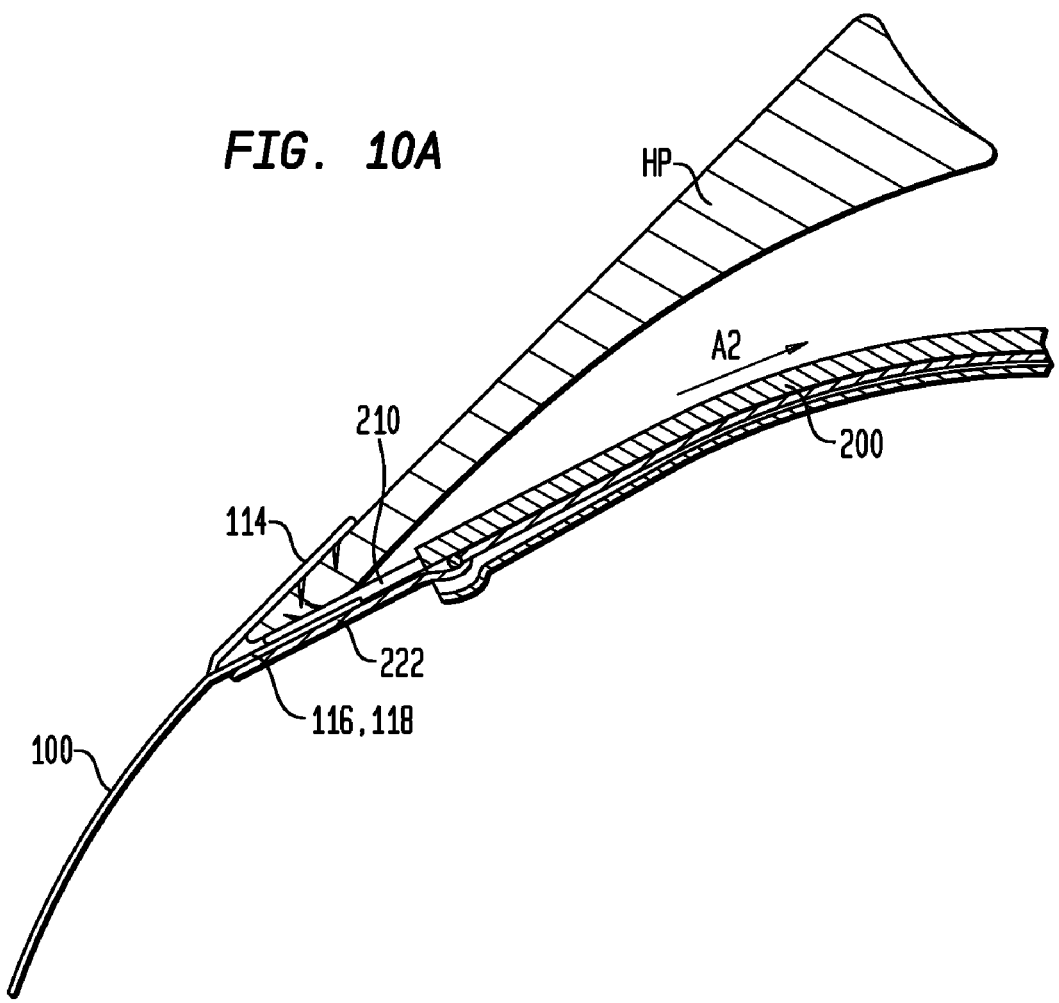
FIGS. 10A-10C show a method of inserting an implant device in a patient using an insertion tool, in accordance with one embodiment of the present invention.
Figures 1, 10A:
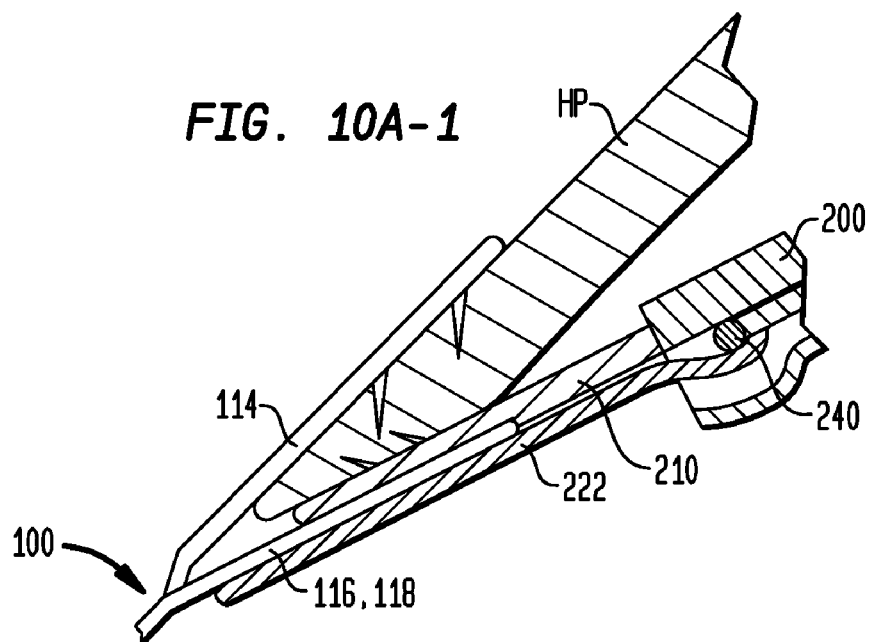

FIGS. 10A-10C and 10A-1 through 10C-1 show a simplified view of how the insertion tool is used for implanting the implant device in the soft palate. Referring to FIG. 10A, after the soft palate implant 100 has been inserted into the surgical opening in the soft palate and while the upper and lower blades 210, 222 hold the implant 100, the insertion tool 200 is moved in a the direction $A_2$ so that the upper anchoring tab 114 overlies the top surface of the hard palate HP and the lower anchoring tabs 116, 118 are positioned under the bottom surface of the hard palate HP.

FIG. 10A-1 shows a magnified cross-sectional view of the soft palate implant 100 and the insertion tool 200 shown in FIG. 10A. The implant 100 includes the upper anchoring tab 114 overlying a top surface of the hard palate HP and the lower anchoring tabs 116, 118 underlying the bottom surface of the hard palate HP. Initially, the lower anchoring tabs 116, 118 remain secured between the upper blade 210 and the lower blade 222 of the insertion tool. The upper and lower blades 210, 222 desirably pinch the lower anchoring tabs 116, 118 therebetween for securing the lower tabs to the distal end of the insertion tool. The push bar 240, which is later used for wedging the lower blade 222 away from the upper blade 210, is preferably in the fully retracted position.

Figure 10B:
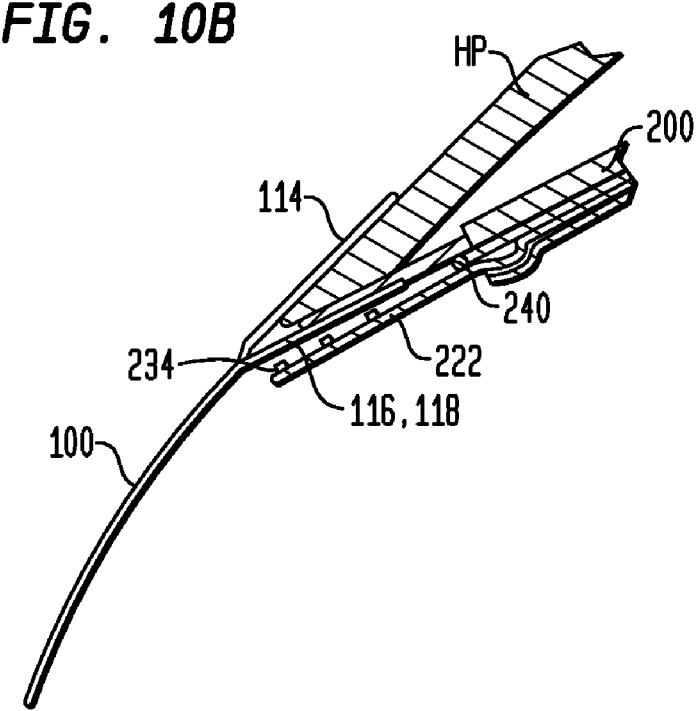
Figures 1, 10B:
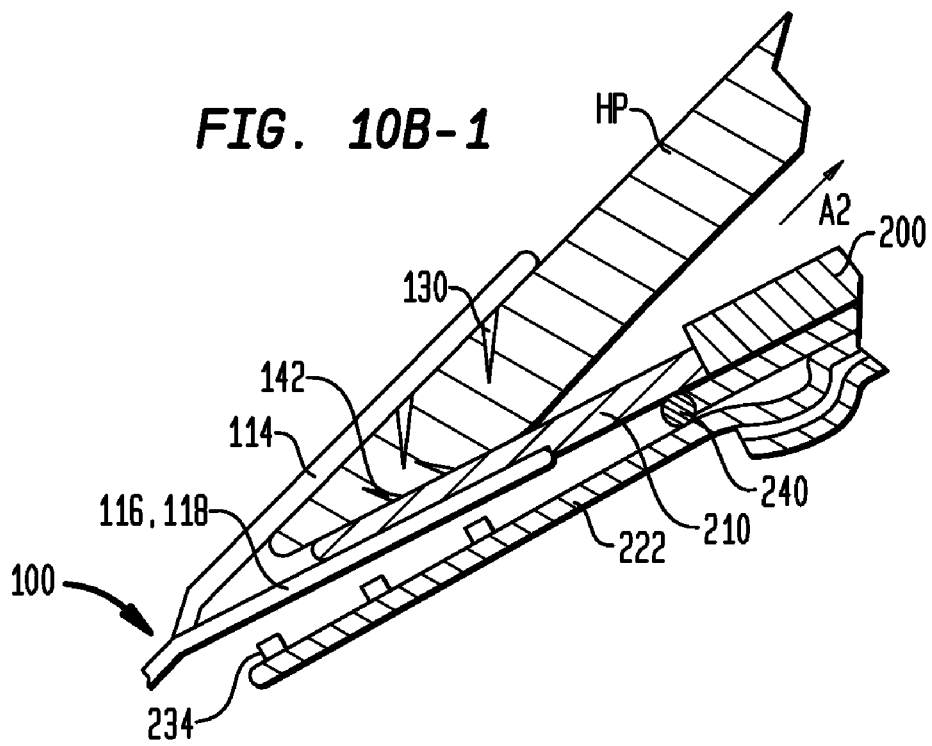

Referring to FIG. 10B, in one embodiment, an actuator at the proximal end of the insertion tool 200 is engaged for moving the push bar 240 in a distal direction designated $D_3$. As the push bar 240 moves in the distal direction, the lower blade 224 is wedged away from the upper blade 210 so that the securing posts 234 on the lower blade 222 are retracted from the through holes extending through the lower anchoring tabs 116, 118.

FIG. 10B-1 shows an expanded view of FIG. 10B, whereby the lower blade 222 of the insertion tool 200 is wedged away from the upper blade 210 by the push bar 240. The posts 234 on the lower blade 222 are retracted from the through holes in the lower anchoring tabs 116, 118 of the implant 100. The barbs on the pair of lower anchoring tabs 116, 118 preferably pass through the slots in the upper blade for engaging the underside of the hard palate HP. After the upper and lower blades 210, 222 have been wedged away from one another for releasing the implant 100, the insertion tool 200 may be retracted in the direction designated $A_2$. After being released from the distal end of the insertion tool, the upper and lowers tabs of the implant 100 preferably bias toward one another for pinching the hard palate HP therebetween. The barbs 130, 142 on the inner surfaces of the opposing upper and lower anchoring tabs 114, 116, 118 preferably bite into the bone of the hard palate HP for anchoring the implant 100 to the hard palate HP.

Figure 10C:
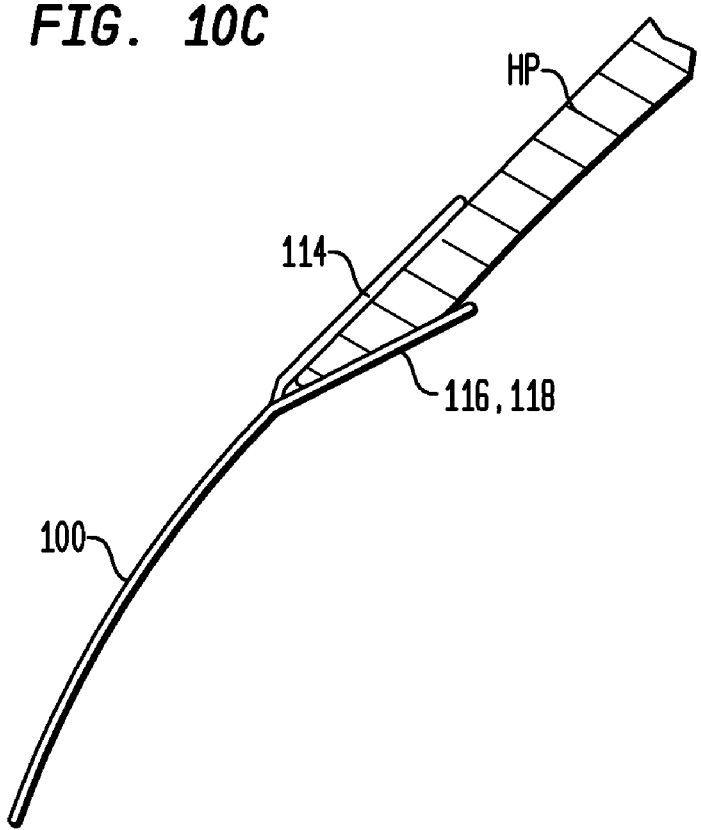
Figures 1, 10C:
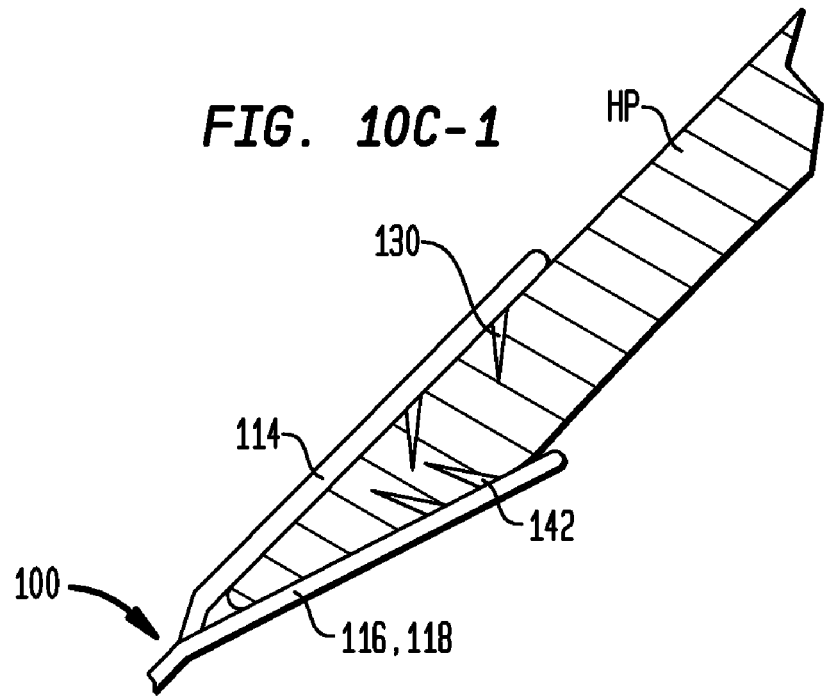

FIGS. 10C and 10C-1 show the implant 100 after it has been anchored to the hard palate HP. The implant 100 includes the upper tab 114 anchored to the top surface of the hard palate HP, and the lower tabs 116, 118 anchored to the underside surface of the hard palate HP. As shown in FIG. 10C-1, the barbs 124 on the upper anchoring tab 114 bite into the upper surface of the hard palate HP, while the barbs 142 on the lower anchoring tabs 116, 118 bite into the underside surface of the hard palate HP. Although barbs are shown for securing the implant to the hard palate, in other embodiments other fastening elements such as screws, pins, tacks, adhesives, wire, and sutures may be used for securing the implant to the hard palate.

Referring to FIG. 11A, some patients have a condition whereby the soft palate SP has a horizontal component H and a vertical component V that is angled relative to the horizontal component. In some instances, the vertical component V may be at an angle that approaches 90° or more relative to the horizontal component H. As is known to those skilled in the art, the existence of the vertical component reduces the size of the opening in the posterior portion of the nasopharynx, which may cause OSA symptoms. In order to change the shape of the soft palate SP and/or provide a soft palate SP having a more continuous arc, an implant as disclosed herein may be implanted into the soft palate of a patient. FIG. 11B shows the soft palate SP of the FIG. 11A after the implant 100 has been implanted therein. The implant 100 includes a proximal end anchored to the hard palate HP of the patient and a distal end that extends to the uvula UV. The implant 100 preferably changes the shape of the soft palate so that it has a more preferred, continuous arc between the hard palate HP and uvula UV. The more continuous arc shape of the soft palate shown in FIG. 11B opens the posterior portion of the nasopharynx and provides more space between the soft palate SP and the posterior pharyngeal wall PPW. During sleep, the implanted device 100 may provide indirect support to the tongue T in an anterior direction for further opening in the posterior portion of the nasopharynx.

Figure 12:
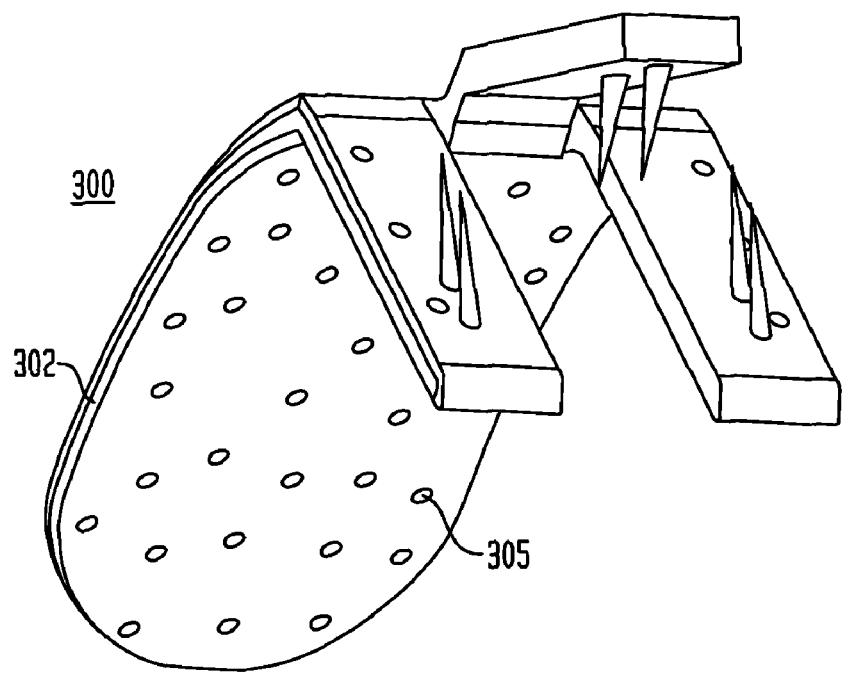
FIG. 12 shows an implant for treating obstructive sleep apnea, in accordance with one embodiment of the present invention.
Figure 13:
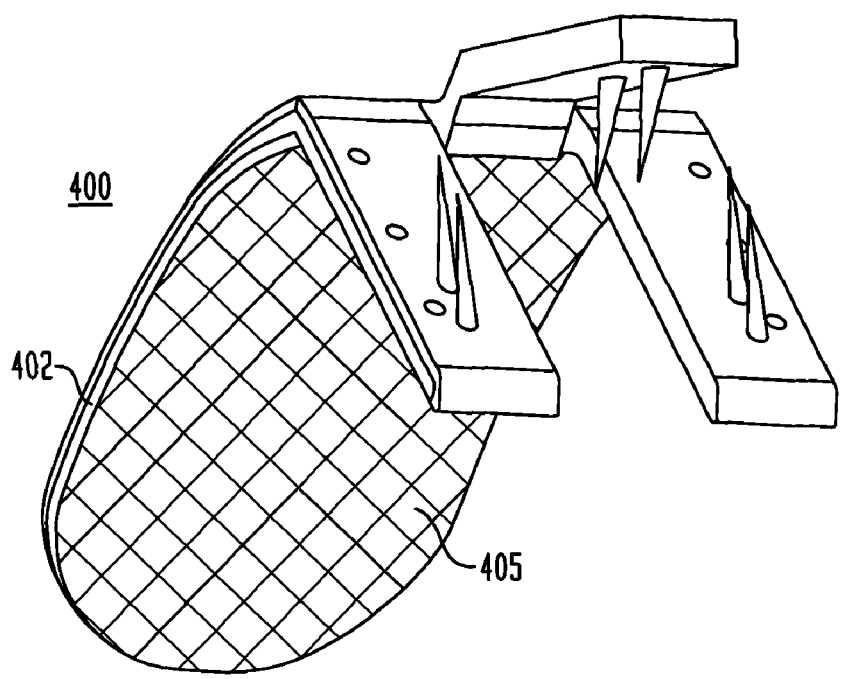
FIG. 13 shows an implant for treating obstructive sleep apnea, in accordance with one embodiment of the present invention.

Referring to FIG. 12, in one embodiment, an implant 300 for supporting and/or changing the shape of the uvula includes a main body 302 and a fastening element provided at a proximal end of the main body. The main body includes a plurality of openings 305 extending therethrough that provide for bone or tissue in-growth. FIG. 13 shows another embodiment of an implant 400 for supporting a uvula including a main body 402 having an outer mesh surface 405 for promoting bone and/or tissue in-growth.

Figure 14:
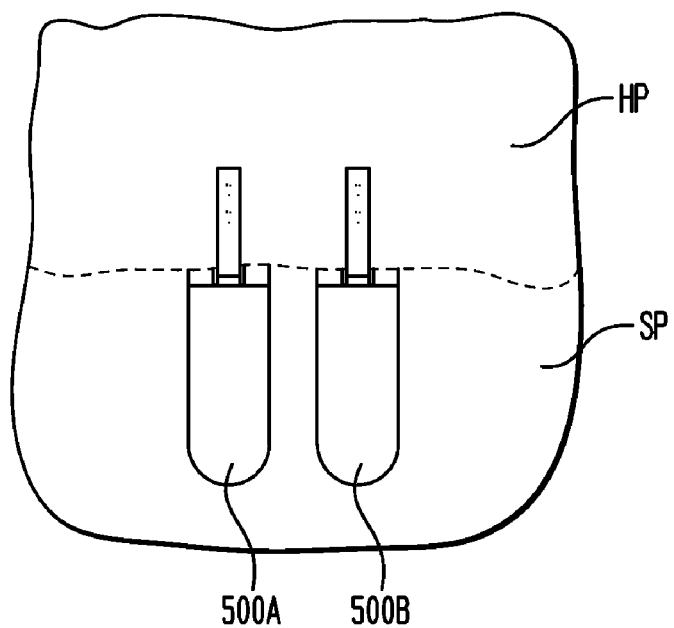
FIG. 14 shows a system for treating obstructive sleep apnea, in accordance with one embodiment of the present invention.
Figure 15:
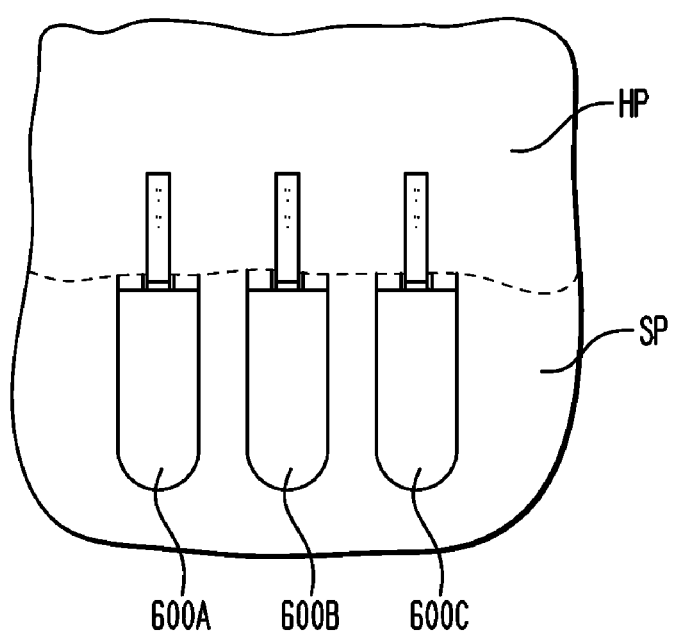
FIG. 15 shows a system for treating obstructive sleep apnea, in accordance with one embodiment of the present invention.

Although the present invention is not limited by any particular theory of operation, it is contemplated that two or more implant devices may be implanted in a soft palate of a patient for supporting and/or changing the shape of the uvula of the patient for treating obstructive sleep apnea. Referring to FIG. 14, in one embodiment, a system for treating obstructive sleep apnea may include a pair of implant devices 500A and 500B implanted in a soft palate SP, whereby each of the implants have distal ends supporting a uvula and proximal ends anchored to a hard palate. Referring to FIG. 15, in one embodiment, a system for treating obstructive sleep apnea may include a plurality of implant devices 600A, 600B, 600C (e.g. three implant devices) that are implanted in a soft palate SP, whereby each of the implants have distal ends supporting a uvula and proximal ends anchored to a hard palate HP. The implants extending through the soft palate may be parallel to one another or may be angled relative to one another. The lengths and/or sizes of the implants may vary. In one embodiment, a first implant may have a first length, and a second adjacent implant may have a second length that is different than the first length.

In other embodiments, fastening elements other than barbs may be used for securing the proximal end of the implant to the hard palate. In one embodiment, one or more screws may be used for securing the implant to a hard palate. In another embodiment, surgical tacks may be used for securing the implant to the hard palate. In yet another embodiment, surgical wire or sutures may be used to securing the implant to the hard palate. Bone needles may also be used for securing the implant to the hard palate.

In one embodiment, the implant may have an outer surface that encourages tissue in-growth so as to stabilize the implant within the tissue and so as to minimize the opportunity for tissue erosion. The outer surface modification may be achieved by texturizing the outer surface, making the implant porous through the addition of holes (e.g. drilled or pierced holes), encapsulating the implant with a braided, surgical mesh, or fleece type material, and/or coating the implant with bone growth stimulating agents such as hydroxyapatite.

Although the present invention is not limited by any particular theory of operation, it is believed that providing a soft tissue implant supported by the distal end of the hard palate provides more positive positioning of the uvula and enables the uvula to provide greater resistance to distal tongue movement than when using implants that are not supported by the hard palate. The soft palate implant of the present invention preferably provides a balanced level of support for the uvula, providing tongue support when needed, but not inhibiting swallowing. The shape changing feature of the implant allows greater uvula support (and thereby tongue support) during times of rest and less support during waking hours. Providing an outer surface on the implant having tissue in-growth capabilities reduces the chance of tissue erosion and provides greater lateral stability to the implant. In one embodiment, the ability to implant the device through the nasal passageways results in the implant location being more cranial, thereby minimizing tongue sensitivity to the presence of the implant. In one embodiment, the implant procedure does not damage the musculature within the soft palate and maintains mucosal surfaces, thereby enabling the natural musculature to continue to provide support in addition to that provided by the implant.

In one embodiment, the soft palate implant may be formed from absorbable materials, non-absorbable materials, or a combination of absorbable and non-absorbable materials. The non-absorbable materials may include polymeric materials such as non-resorbable polymers, silicone, polyethylene terephalate, polytetrafluoroethylene, polyurethane and polypropylene, nitninol, stainless steel, and/or composite materials. Suitable resorbable polymers may include polylactide, polyglycolide copolymers, polycaprolactone, and/or collagen. The implant may also include a biocompatible metal or alloy.

The present invention provides a number of advantages over prior art methods and devices used for treating obstructive sleep apnea syndrome and hypopnea. First, the methods, systems and devices disclosed herein provide for simple surgical procedures that are minimally invasive. Typically, the methods, systems and devices disclosed herein may be utilized during an outpatient procedure. In addition, the methods, systems and devices disclosed herein provide both immediate and long term results for treating obstructive sleep apnea syndrome and hypopnea. Moreover, the methods, systems and devices disclosed herein do not require a significant level of patient compliance.

In addition, the present invention does not anchor the tongue to a fixed hard structure, such as the mandible. Thus, the present invention is significantly less likely to affect swallowing or speech, thereby providing a great improvement over prior art devices, systems and methods. The present invention also preferably uses materials having long-term biocompatibility.

Although various embodiments disclosed herein relate to use in humans, it is contemplated that the present invention may be used in all mammals, and in all animals having air passages. Moreover, the methods, systems and devices disclosed herein may incorporate any materials that are biocompatible, as well as any solutions or components that minimize rejection, enhance tissue ingrowth, enhance the formation of mucosal layers, and improve acceptance of the device by a body after the device has been implanted.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A system for treating obstructive sleep apnea comprising:
   a body implantable in a soft palate;
   a fastening element at a proximal end of said body for connecting said body with a hard palate, said fastening element including an upper tab protecting from the proximal end of said body for being secured to a top surface of said hard palate and at least one lower tab protecting from the proximal end of said body for being secured to a bottom surface of said hard palate, wherein said upper tab and said at least one lower tab oppose one another and are normally biased toward one another.

2. The system as claimed in claim 1, wherein said body is curved.

3. The system as claimed in claim 2, wherein said curved body has a convex top surface and a concave bottom surface.

4. The system as claimed in claim 1, wherein said upper tab and said at least one lower tab have tissue engaging barbs adapted for biting into said hard palate for securing said body to said hard palate.

5. The system as claimed in claim 1, wherein said at least one lower tab comprises a pair of lower tabs, and wherein said upper tab and said pair of lower tabs oppose one another and are normally biased toward one another for engaging said hard palate.

6. The system as claimed in claim 5, wherein said upper tab has tissue engaging barbs that extend toward said lower tabs and that are adapted for biting into a top surface of said hard palate, wherein each of said lower tabs has tissue engaging barbs that extend toward said upper tab and that are adapted for biting into a bottom surface of said hard palate, and wherein each of said lower tabs includes holes formed therein that are adapted for securing said lower tabs to a distal end of an insertion instrument.

7. The system as claimed in claim 6, wherein said upper tab is centered between said two lower tabs.

8. The system as claimed in claim 6, further comprising an insertion tool having a distal end including an upper blade and an opposing lower blade adapted to secure said lower tabs therebetween, wherein said upper blade has aligned slits extending from a leading end to a trailing end of said upper blade that are adapted to receive said barbs on said respective lower tabs, and wherein said lower blade has posts projecting therefrom that are insertable into said holes on said lower tabs for securing said lower tabs to said distal end of said insertion tool.

9. The system as claimed in claim 1, wherein said body has a surface adapted to promote tissue in-growth.

10. The system as claimed in claim 9, wherein said tissue in-growth promoting surface is selected from the group of outer surfaces consisting of a textured surface, a porous surface, a braided surface, a mesh surface, a fleece surface, and a coating for inducing bone-growth.

11. The system as claimed in claim 1, wherein said body is selected from the group of materials consisting of nitinol, stainless steel, biocompatible polymers, temperature-sensitive materials, and shape memory materials.

12. An implant for supporting a uvula for treating obstructive sleep apnea comprising:
    a body implantable in a soft palate, said body having a distal end and a proximal end;
    a fastening element adjacent the proximal end of said body for fastening said body to a hard palate, said fastening element including an upper tab and a pair of lower tabs opposing said upper tab, said upper tab and said lower tabs protecting from said proximal end of said body, said upper tab having barbs that extend toward said pair of lower tabs and each of said lower tabs having barbs that extend toward said upper tab, wherein said upper tab and said pair of lower tabs are normally biased toward one another for engaging the respective top and bottom surfaces of said hard palate.

13. The implant as claimed in claim 12, wherein each of said lower tabs has holes formed therein that are adapted for being engaged by posts on a distal end of an insertion instrument.

14. The implant as claimed in claim 12, wherein said body is curved.

15. The implant as claimed in claim 14, wherein said curved body has a convex top surface and a concave bottom surface.

* * * * *